US011529435B2

(12) United States Patent
Shen et al.

(10) Patent No.: US 11,529,435 B2
(45) Date of Patent: Dec. 20, 2022

(54) NON-FIBROUS POROUS FILM AND METHOD FOR TISSUE ADHESION

(71) Applicant: INDUSTRIAL TECHNOLOGY RESEARCH INSTITUTE, Hsinchu (TW)

(72) Inventors: Hsin-Hsin Shen, Hsinchu County (TW); Ming-Chia Yang, Taipei (TW); Chia-Chi Ho, Zhubei (TW); Fang-Jie Jang, Keelung (TW); Che-Yu Ou, Kaohsiung (TW); Chi-Hsiang Liao, Miaoli County (TW); Brian Hsu, Hsinchu (TW); Tai-Horng Young, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 78 days.

(21) Appl. No.: 17/308,547

(22) Filed: May 5, 2021

(65) Prior Publication Data

US 2021/0322625 A1 Oct. 21, 2021

Related U.S. Application Data

(60) Division of application No. 15/855,694, filed on Dec. 27, 2017, now Pat. No. 11,027,040, which is a (Continued)

(30) Foreign Application Priority Data

Nov. 16, 2017 (TW) .................................. 106139675

(51) Int. Cl.
*A61L 24/00* (2006.01)
*A61L 24/04* (2006.01)

(52) U.S. Cl.
CPC ....... *A61L 24/0036* (2013.01); *A61L 24/0015* (2013.01); *A61L 24/0042* (2013.01); (Continued)

(58) Field of Classification Search
None
See application file for complete search history.

(56) References Cited

U.S. PATENT DOCUMENTS 5,952,120 A 9/1999 Yu et al.
6,143,211 A 11/2000 Mathiowitz et al.
(Continued)

FOREIGN PATENT DOCUMENTS

CN 1183051 A 5/1998
CN 1569253 A 1/2005
(Continued)

OTHER PUBLICATIONS

English Language Translation of KR 2016 0001071. (Year: 2016).*
(Continued)

*Primary Examiner* — Dominic Lazaro
(74) *Attorney, Agent, or Firm* — Birch, Stewart, Kolasch & Birch, LLP

(57) ABSTRACT

The present disclosure provides a method for manufacturing a porous film, including: preparing a polymer mixture solution, wherein the polymer mixture solution includes polycaprolactone and at least one hydrophobic polymer; adding solid particles as a dispersing agent to the polymer mixture solution and mixing the solid particles with the polymer mixture solution, wherein the amount of solid particles added is enough to convert the polymer mixture solution into a solid mixture; drying the solid mixture to form a film; and washing the film with a washing fluid to remove the solid particles from the film to form the porous film, wherein the weight ratio of the polycaprolactone to the at least one
(Continued)

hydrophobic polymer is about 1:0.1-10, and wherein the weight ratio of the polycaprolactone and the at least one hydrophobic polymer to the solid particles is about 1:0.01-250.

24 Claims, 12 Drawing Sheets

Related U.S. Application Data continuation-in-part of application No. 15/394,001, filed on Dec. 29, 2016, now abandoned.

(52) U.S. Cl.
CPC ......... *A61L 24/0089* (2013.01); *A61L 24/043* (2013.01); *A61L 2300/216* (2013.01)

(56) References Cited

U.S. PATENT DOCUMENTS

| | | | |
|---|---|---|---|
| 6,207,053 | B1 | 3/2001 | Carroll et al. |
| 6,368,742 | B2 | 4/2002 | Fisher et al. |
| 6,838,528 | B2 | 1/2005 | Zhao |
| 8,377,241 | B2 * | 2/2013 | Farnsworth ............. A61L 27/56 156/181 |
| 8,974,815 | B2 | 3/2015 | Chu et al. |
| 9,439,416 | B2 | 9/2016 | Franklin et al. |
| 2003/0146532 | A1 | 8/2003 | Chen et al. |
| 2012/0225039 | A1 | 9/2012 | Li et al. |
| 2013/0045266 | A1 | 2/2013 | Choi et al. |
| 2016/0022878 | A1 | 1/2016 | Young et al. |

FOREIGN PATENT DOCUMENTS

| | | | |
|---|---|---|---|
| CN | 101176799 A | | 5/2008 |
| CN | 101378791 A | | 3/2009 |
| CN | 101703811 A | | 5/2010 |
| CN | 101854925 A | | 10/2010 |
| CN | 106139230 A | | 11/2016 |
| KR | 2016 0001071 A | * | 1/2016 |
| KR | 10-1617434 B1 | | 5/2016 |
| TW | 201603837 A | | 2/2016 |

OTHER PUBLICATIONS

Chinese Office Action and Search Report, dated Jun. 28, 2020, for Chinese Application No. 201711381651.X.
KR 20160001071, English language translation from Espacenet, Published Jan. 2016, Cho Min Kyung.
McDonald et al., "In vitro Degradation and Drug Release from Polymer Blends Based on poly(DL-lactide), poly(L-lactide-glycolide) and poly(ε-caprolactone)," J Mater Sci, vol. 45, 2010, pp. 1284-1292.
Taiwanese Office Action and Search Report, dated Aug. 7, 2017 for Taiwanese Application No. 105143829.
Zhu et al., "Fabrication and Properties of PLGA/PCL Composites," Materials Review, vol. 18, Sep. 28, 2014, pp. 51-55, with an English abstract.

* cited by examiner

| Operation for implanting a film of the present disclosure in the experimental group | Day 0 of implantation of the film in the experimental group |
|---|---|
|  |  |

3 months after implanting the film of the present disclosure in the experimental group 3 months after implanting the film of the present disclosure in the control group

NON-FIBROUS POROUS FILM AND METHOD FOR TISSUE ADHESION

CROSS REFERENCE TO RELATED APPLICATION

This application is a Divisional of pending U.S. patent application Ser. No. 15/855,694, filed Dec. 27, 2017 and entitled "METHOD FOR MANUFACTURING A POROUS FILM, POROUS FILM AND METHOD FOR TISSUE ADHESION", which is a Continuation-In-Part of pending prior application Ser. No. 15/394,001, filed Dec. 29, 2016, entitled "METHOD FOR MANUFACTURING A POROUS FILM AND POROUS FILM AND METHOD FOR MAKING TISSUE ADHESION" and is based on, and claims priority from, Taiwan Application Serial Number 106139675, filed on Nov. 16, 2017, the disclosure of which is hereby incorporated by reference herein in its entirety.

TECHNICAL FIELD

The present disclosure relates to a non-fibrous porous film and method for tissue adhesion.

BACKGROUND

At present, the main surgical method for accomplishing adhesion uses a physical injury or a sclerosing agent to cause serious tissue inflammation, which results in adhesion. For example, pleurodesis can let parietal pleura connect to visceral pleura to eliminate a pleural space, thereby preventing the formation of pleural effusion and pneumothorax.

However, using the method detailed above, not only do patients need a longer time to heal, but they will experience pain.

Furthermore, at present, commercial surgical meshes are mostly used for reinforcing or joining an injury or a surgical wound, and as barriers between organs, and they cannot be used effectively in tissue adhesion. Commercial surgical mesh is a soft mesh formed by weaving single material made of fibers with a high density and a high hardness, and its surface is not rough. Therefore, when a commercial surgical mesh is used to perform tissue adhesion, it is difficult to attach, and tissues are less likely to grow therein.

Therefore, at present, what is needed is a method of manufacturing a film which is capable of uniformly mixing different kinds of polymers and keeping the physicochemical properties of the different polymers intact in order to produce a film that is suitable to a method of tissue adhesion. Moreover, in this method of manufacturing a film, a drug for promoting adhesion, tissue repair, and treatment can also be used.

SUMMARY

The present disclosure provides a non-fibrous porous film, which is manufactured by a method for manufacturing a non-fibrous porous film, wherein the method for manufacturing a non-fibrous porous film comprises: preparing a polymer mixture solution, wherein the polymer mixture solution comprises: polycaprolactone (PCL); and at least one hydrophobic polymer, which is selected from a group consisting of polylactic acid (PLA), poly(lactic-co-glycolic acid (PLGA), poly(glycolic acid) (PGA), polyhydroxybutyrate (PHB), polydioxanone (PDS), poly(propylene fumarate) (PPF), polyanhydrides, polyacetals, poly(ortho esters), polycarbonates, polyurethanes, polyphosphazenes and polyphosphoester, wherein the molecular weight of the at least one hydrophobic polymer is about 10K-800K; adding solid particles as a dispersing agent to the polymer mixture solution and mixing the solid particles with the polymer mixture solution, wherein the amount of solid particles added is enough to convert the polymer mixture solution into a solid mixture, wherein the particle size of the solid particles is about 50-250 μm; drying the solid mixture to form a film; and washing the film with a washing fluid to remove the solid particles from the film to form a porous film, wherein the weight ratio of the polycaprolactone to the at least one hydrophobic polymer is about 1:0.1 to 1:10, and wherein the weight ratio of the polycaprolactone and the at least one hydrophobic polymer to solid particles is about 1:0.01 to 1:250, and wherein the real density of the non-fibrous porous film is $1.5\text{-}5.0\times10^{-3}$ g/cm$^2$.

The present disclosure further provides non-fibrous porous film, which is composed of a polymer mixture, wherein the polymer mixture comprises: polycaprolactone; and at least one hydrophobic polymer, which is selected from a group consisting of polylactic acid (PLA), poly(lactic-co-glycolic acid (PLGA), poly(glycolic acid) (PGA), polyhydroxybutyrate (PHB), polydioxanone (PDS), poly(propylene fumarate) (PPF), polyanhydrides, polyacetals, poly(ortho esters), polycarbonates, polyurethanes, polyphosphazenes and polyphosphoester, wherein the molecular weight of the at least one hydrophobic polymer is about 10K-800K, wherein the weight ratio of the polycaprolactone to the at least one hydrophobic polymer is about 1:0.1 to 10, and wherein the porosity of the non-fibrous porous film is 80-99%, and the roughness of the non-fibrous porous film is 10-500 μm, wherein the real density of the non-fibrous porous film is $1.5\text{-}5.0\times10^{-3}$ g/cm$^2$.

The present disclosure provides a method for tissue adhesion, comprising: applying the non-fibrous porous film mentioned above to a location in a body which needs tissues to adhere to each other to promote tissue-adhesion.

The present disclosure further provides a use of any one of the preceding porous films for the manufacture of a film used in a tissue-adhesion method.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION

Figure 1A:
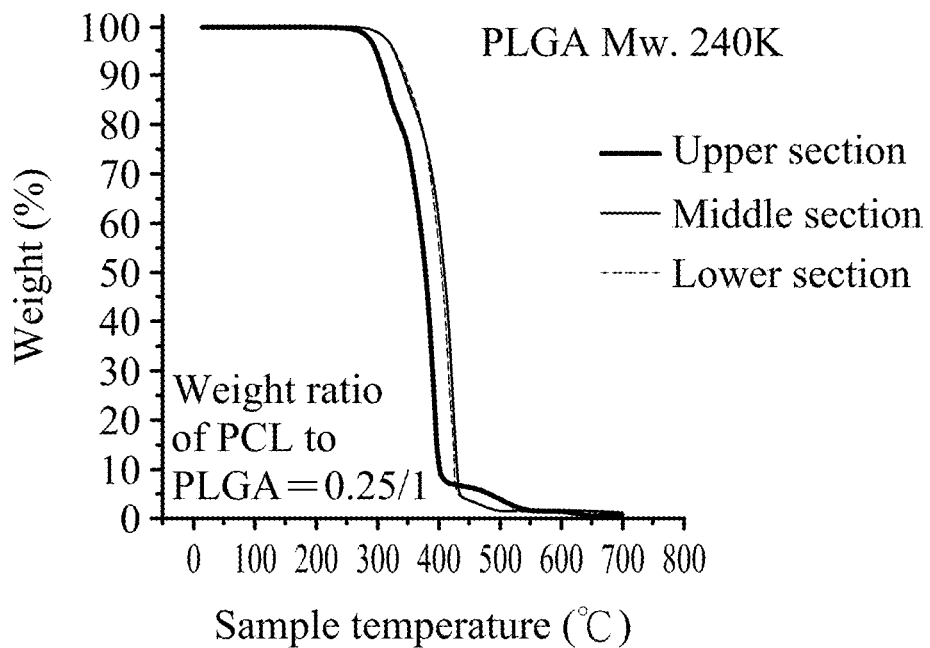
FIG. 1A shows thermogravimetric analysis results of the film prepared by a process in which the molecular weight of the poly(lactic-co-glycolic acid) is 240K, and the weight ratio of the polycaprolactone to the poly(lactic-co-glycolic acid) is 0.25:1, at different locations.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In one aspect of the present disclosure, a method for manufacturing a porous film is provided. A film manufactured by the method for manufacturing a porous film has a physicochemical property of the ability to uniformly mix more than two kinds of hydrophobic polymer.

In the method of the present disclosure, control of the polymer blending ratio allows the degradation time of the formed film in the body to be controlled, and have properties of high porosity, high roughness, etc. Moreover, the method of the present disclosure lets a formed film have a real density that is substantially lower than its theoretical density, and can obtain a film which is of low density, is light and thin, and can be attached evenly. Furthermore, since a film formed by the method of the present disclosure is light and thin, it is easy to be folded, and can easily be operated and placed into a body. In addition, since a film formed by the method of the present disclosure has such properties as low density, lightness, and thinness, it is capable of floating on the tissue fluid of the surface of a tissue or an organ, and evenly attach thereon.

A film formed by the method of the present disclosure can be applied to a surgical method for tissue adhesion to promote tissue adhesion, and during repair and adhesion of tissue, since a film formed by the method of the present disclosure has pores which communicate with each other and a thin thickness, the film is beneficial in that different cells or tissues may penetrate therein and grow, and the film promotes rapid tissue repair and adhesion and is capable of increasing the mechanical strength of repairing tissues and adhesive tissues.

In addition, a film formed by the method of the present disclosure may have the ability to encapsulate and release drugs while the drug encapsulated by the film is capable of decreasing the probability of inflammation or infection and accelerate the healing of an affected region.

The preceding method for manufacturing a porous film, may include the following steps, but it is not limited thereto.

First, a polymer mixture solution is prepared, and the polymer mixture solution may include, but is not limited to, polycaprolactone and at least one hydrophobic polymer. In the polymer mixture solution, the weight ratio of the polycaprolactone to the at least one hydrophobic polymer may be about 1:0.1-10, but it is not limited thereto.

The molecular weight of the hydrophobic polymer mentioned above may be about 10K-800K. In one embodiment, the molecular weight of the hydrophobic polymer mentioned above may be about 8K-240K.

Moreover, examples of the hydrophobic polymer mentioned above may include polylactic acid (PLA), poly(lactic-co-glycolic acid (PLGA), poly(glycolic acid) (PGA), polyhydroxybutyrate (PHB), polydioxanone (PDS), poly(propylene fumarate) (PPF), polyanhydrides, polyacetals, poly(ortho esters), polycarbonates, polyurethanes, polyphosphazenes, polyphosphoester and combinations thereof, but they are not limited thereto. In one embodiment, the hydrophobic polymer mentioned above may be poly(lactic-co-glycolic acid), and the molecular weight thereof may be about 10K-800K.

The foregoing polymer mixture solution may be prepared by a method, and this method may include dissolving the polycaprolactone in a first solvent to form a first solution, and dissolving the at least one hydrophobic polymer in a second solvent to form a second solution, and then mixing the first solution with the second solution to form said polymer mixture solution. The foregoing first solvent and the foregoing second solvent may be the same or different.

Examples of the first solvent and the second solvent may include an alkane, an alkene, an alcohol, an aldehyde, an amine, an ester, an ether, a ketone, an aromatic hydrocarbons, a hydrogenated hydrocarbon, a terpene hydrocarbon, a haloalkane, heterocyclic compound, a nitrogen-containing compound, and a sulfur compound, but they are not limited thereto. In one embodiment, the foregoing first solvent may include dichloromethane, chloroform or acetone, but it is not limited thereto, and the foregoing second solvent may include, but is not limited to, dichloromethane, chloroform or acetone.

Alternatively, the preceding polymer mixture solution may be prepared by another method, and this method may include dissolving the polycaprolactone and the hydrophobic polymer mentioned above in a solvent to form the polymer mixture solution. Examples of the solvent mentioned herein may include an alkane, an alkene, an alcohol, an aldehyde, an amine, an ester, an ether, a ketone, an aromatic hydrocarbons, a hydrogenated hydrocarbon, a terpene hydrocarbon, a haloalkane, heterocyclic compound, a nitrogen-containing compound, and a sulfur compound, but they are not limited thereto. In one embodiment, said solvent may include dichloromethane, chloroform or acetone.

Next, solid particles as a dispersing agent are added to the polymer mixture solution mentioned above and mixed with the polymer mixture solution mentioned above, wherein the amount of solid particles added is enough to convert the polymer mixture solution into a solid mixture and let the polycaprolactone and the hydrophobic polymer uniformly disperse in the polymer mixture solution. Moreover, in the solid mixture, the weight ratio of the polycaprolactone and the hydrophobic polymer to solid particles is about 1:0.01-250, and the particle size of the aforementioned solid particles is about 50-250 µm. In one embodiment, the particle size of the preceding solid particles may be about 90-150 µm.

The aforementioned solid particles may include chloride particles, oxide particles, hydroxide particles, fluoride particles, nitrate particles, sulfate particles, nitrite particles, ammonium salt, phosphate particles, silicate particles, carbonate particles, oxalate particles, or a combination thereof, but it is not limited thereto. In one embodiment, the preceding solid particles are sodium chloride particles. Furthermore, in this embodiment, the particle size of the sodium chloride particles may be about 90-150 µm.

In the method for manufacturing a film of the present disclosure, in one embodiment, the at least one hydrophobic polymer mentioned above may be poly(lactic-co-glycolic acid), and the above-mentioned solid particles may be sodium chloride particles. Moreover, in this embodiment, the molecular weight of the poly(lactic-co-glycolic acid) may be about 8K-240K. Moreover, in this embodiment, the particle size of the sodium chloride particle may be about 90-150 µm. In addition, in this embodiment, the weight ratio of the polycaprolactone to the poly(lactic-co-glycolic acid) may be about 1:0.1-10, and the weight ratio of the polycaprolactone and the poly(lactic-co-glycolic acid) to the sodium chloride may be about 1:0.01-250.

In addition, in this embodiment, the foregoing polymer mixture solution may be prepared by a method, this method may include dissolving polycaprolactone in a first solvent to form a first solution, and dissolving the poly(lactic-co-glycolic acid) in a second solvent to form a second solution, and then mixing the first solution with the second solution to form said polymer mixture solution.

In addition, the first solvent and the second solvent mentioned in this embodiment, may be the same or different. Examples for the first may include dichloromethane, chloroform and acetone, but they are not limited thereto. Moreover, the second solvent mentioned above may include, but is not limited to, dichloromethane, chloroform or acetone. In one specific embodiment, the first solvent and the second solvent are the same, for example, the first solvent and the second solvent may both be dichloromethane.

In one embodiment, the polymer mixture solution, in addition to the polycaprolactone and at least one hydrophobic polymer, may further include at least one hydrophobic drug. In this embodiment, the weight ratio of the polycaprolactone, the at least one hydrophobic polymer and the at least one hydrophobic drug to solid particles is about 1:0.5-10.

Furthermore, the molecular weight of the at least one hydrophobic drug mentioned above may be about 50K-100K, but it is not limited thereto. Examples of the at least one hydrophobic drug mentioned above, may include, citral, nitrogen mustard, cisplatin, paclitaxel, and combinations thereof, but they are not limited thereto.

Moreover, in the embodiment in which the polymer mixture solution, in addition to the polycaprolactone and the at least one hydrophobic polymer, may further include at least one hydrophobic drug, a method for preparing the polymer mixture solution mentioned above may include the following steps, but it is not limited thereto.

The polycaprolactone is dissolved in a first solvent to form a first solution, and the at least one hydrophobic polymer is dissolved in a second solvent to form a second solution, and then mixing the first solution with the second solution to form said polymer mixture solution, wherein the foregoing first solvent and the foregoing second solvent may be the same or different.

Next, the first solution is mixed with the second solution to form the polymer mixture solution.

Examples of the first solvent and the second solvent may include an alkane, an alkene, an alcohol, an aldehyde, an amine, an ester, an ether, a ketone, an aromatic hydrocarbons, a hydrogenated hydrocarbon, a terpene hydrocarbon, a haloalkane, heterocyclic compound, a nitrogen-containing compound, and a sulfur compound, but they are not limited thereto. In one embodiment, the first solvent or the second solvent may include dichloromethane, chloroform or acetone. In one specific embodiment, the first solvent and the second solvent are the same, for example, the first solvent and the second solvent may both be dichloromethane.

Furthermore, in one specific embodiment, the polymer mixture solution may include polycaprolactone, poly(lactic-co-glycolic acid) and citral. In addition, in the specific embodiment, the solid particles mentioned above may be sodium chloride particles.

After that, the above-mentioned solid mixture is dried to form a film.

In the method for manufacturing a film of the present disclosure, a manner for drying the above-mentioned solid mixture has no particular limitation, only if the solid mixture is able to form a film. In one embodiment, the solid mixture may be poured on a plate, and then scraped with a scraper to perform a film scraping procedure, and after that, dried to form a film. The speed for film scraping may be about 1-1000 mm/second, but it is not limited thereto. Moreover, the thickness of the scraper may be about 1-3000 μm, but it is not limited thereto.

After the film is formed, the film is washed with a washing fluid to remove the solid particles from the film, to form a porous film.

Examples of the preceding washing fluid may include, but are not limited to, water, hydrochloric acid, acetic acid, phosphoric acid, and peroxy acid. In one embodiment, the preceding washing fluid washing fluid may be water.

Moreover, the roughness of a porous film formed by any one method for manufacturing a film of the present disclosure may be about 10-500 μm, such as 90-200 μm. The porosity of a porous film formed by any one method for manufacturing a film of the present disclosure may be 80-99%, such as 80-90%.

Any one method for manufacturing a film of the present disclosure can form a low-density film having a real density that is lower than its theoretical density. The density (real density) of a porous film formed by any one method for manufacturing a film of the present disclosure may be $1.5\text{-}5.0\times10^{-3}$ g/cm$^2$, such as $2.5\text{-}3.3\times10^{-3}$ g/cm$^2$, but it is not limited thereto. In one embodiment, the density (real density) of a porous film formed by any one method for manufacturing a film of the present disclosure may be $2.5\text{-}3.3\times10^{-3}$ g/cm$^2$.

Any one method for manufacturing a film of the present disclosure can form a light and thin film. The thickness of a porous film formed by any one method for manufacturing a film of the present disclosure may be about 10-1000 μm, such as 50-500 μm, 100-200 μm, but it is not limited thereto. In one embodiment, the thickness of a porous film formed by any one method for manufacturing a film of the present disclosure may be about 120-190 μm. Since a film formed by any one method for manufacturing a film of the present disclosure has the properties of lightness and thinness, it is easy to operate and easy to fold.

In another aspect of the present disclosure, a porous film formed by any one method for manufacturing a film of the present disclosure is provided.

The porosity of the porous film may be 80-99%. In one embodiment, the porosity of the porous film may be 80-90%. The roughness of the porous film mentioned above may be 10-500 μm, such as 90-200 μm.

Furthermore, the density (real density) of the porous film mentioned above may be about $1.5\text{-}5.0\times10^{-3}$ g/cm$^2$, such as $2.5\text{-}3.3\times10^{-3}$ g/cm$^2$, but it is not limited thereto. In one embodiment, the density (real density) of the porous film mentioned above may be $2.5\text{-}3.3\times10^{-3}$ g/cm$^2$.

In addition, the thickness of the porous film mentioned above may be about 10-1000 μm, such as 50-500 μm, 100-200 μm, but it is not limited thereto. In one embodiment, the thickness of the porous film mentioned above may be about 120-190 μm.

In another aspect of the present disclosure, a porous film having properties of high porosity, high roughness, low density, lightness and thinness, etc., and having the ability to be evenly attached, is provided. Since the film is light and thin, it is easy to fold and easy to operate for placement into a body. Moreover, since the film has the properties of low density, lightness, and thinness, it is capable of floating on the tissue fluid of the surface of a tissue or an organ, and being evenly attached thereon.

The film can be applied to a surgical method for tissue adhesion to promote tissue adhesion. Moreover, since the film has pores which communicate with each other and a thin thickness, the film is beneficial in that different cells or tissues can penetrate therein and grow, and it promotes rapid tissue repair and adhesion and is capable of increasing the mechanical strength of repairing tissues and adhesive tissues.

Moreover, the porosity of this porous film may be 80-99%, but it is not limited thereto. In one embodiment, the porosity of the porous film may be 80-90%. The roughness of this porous film may be 10-500 μm, such as 90-200 μm.

Furthermore, the density (real density) of the porous film may be about $1.5\text{-}5.0\times10^{-3}$ g/cm$^2$, such as $2.5\text{-}3.3\times10^{-3}$ g/cm$^2$, but it is not limited thereto. In one embodiment, the density (real density) of the porous film may be $2.0\times10^{-3}$ g/cm$^2$.

In addition, the thickness of the porous film may be about 10-1000 μm, such as 50-500 μm, 100-200 μm, but it is not limited thereto. In one embodiment, the thickness of the porous film may be 120-190 μm.

The porous film mentioned above may be composed of a polymer mixture, and said polymer mixture may include polycaprolactone and at least one hydrophobic polymer, but it is not limited thereto.

In the above-mentioned polymer mixture, the weight ratio of the polycaprolactone to the hydrophobic polymer may be about 1:0.1-10, but it is not limited thereto.

Moreover, the molecular weight of the at least one hydrophobic polymer mentioned above may be about 10K-800K. In one embodiment, the molecular weight of the at least one hydrophobic polymer mentioned above may be about 8K-240K Examples of the at least one hydrophobic polymer mentioned above, may include polylactic acid (PLA), poly(lactic-co-glycolic acid (PLGA), poly(glycolic acid) (PGA), polyhydroxybutyrate (PHB), polydioxanone (PDS), poly(propylene fumarate) (PPF), polyanhydrides, polyacetals, poly(ortho esters), polycarbonates, polyurethanes, polyphosphazenes, polyphosphoester, and combinations thereof, but they are not limited thereto.

In one embodiment, the at least one hydrophobic polymer mentioned above may be poly(lactic-co-glycolic acid). Moreover, in this embodiment, the molecular weight of the poly(lactic-co-glycolic acid) may be about 8K-240K. Furthermore, in this embodiment, the weight ratio of polycaprolactone to the poly(lactic-co-glycolic acid) may be about 1:0.1-10.

Moreover, in this embodiment, the porosity of the porous film may be 80-99%, such as 80-90%. The roughness may be 10-500 μm, such as 90-200 μm. Furthermore, the density (real density) of this porous film may be 1.5-5.0 g/cm², such as 2.5-3.3×10⁻³ g/cm². The thickness of the porous film may be about 10-1000 μm, such as 50-500 μm, 100-200 μm, but it is not limited thereto. In one specific embodiment, the thickness of the porous film may be about 120-190 μm.

In another embodiment, the polymer mixture which constitutes the porous film, in addition to the polycaprolactone and the at least one hydrophobic polymer, may further include at least one hydrophobic drug. The weight ratio of the polycaprolactone to the at least one hydrophobic drug may be about 1:0.05-5, but it is not limited thereto. For example, the weight ratio of the polycaprolactone to the at least one hydrophobic drug may be 1:0.1-1.

The molecular weight of the at least one hydrophobic drug mentioned above may be about 50K-100K, but it is not limited thereto. Examples of the at least one hydrophobic drug mentioned above may include citral, nitrogen mustard, cisplatin, paclitaxel and combinations thereof, but they are not limited thereto.

Furthermore, in the embodiment, the polymer mixture constitutes a porous film, in addition to the polycaprolactone and the hydrophobic polymer, and it may further include at least one hydrophobic drug; and in this embodiment, the porosity of the porous film may be 80-99%, such as 80-90%. Moreover, the roughness may be 10-500 μm, such as 90-200 μm. Furthermore, the density of this porous film may be 1.5-5.0×10⁻³ g/cm², such as 2.5-3.3×10⁻³ g/cm². In addition, the thickness of the porous film may be about 10-1000 μm, such as 50-500 μm, 100-200 μm, but it is not limited thereto. In one embodiment, the thickness of the porous film may be about 120-190 μm.

Any film of the present disclosure mentioned above is capable of fusing two kinds of hydrophobic polymer and is biodegradable, and is capable of floating on the tissue fluid of the surface of a tissue or an organ, and evenly attach thereon due to its lightness and thinness and low density, and thus it can be simply operated in a minimally invasive surgery. The interior of the film can assist tissue metabolism and nutrient transfer due to its high porosity, and can let cells grow into the film to promote adhesion. Therefore, any one of the preceding porous films of the present disclosure can be applied to a tissue adhesive method to promote tissue adhesion. Furthermore, holes in any of the preceding porous films of the present disclosure have the physical effect of raising biocompatibility, and macroscopic holes can provide high oxygen permeability to the repaired region. Such macroscopic holes have a swelling space which can absorb redundant exudate to provide wettability to the repaired region, which assists the repaired region to heal fast. It also allows the tissue to grow through the holes during healing and increase the repairing effect. In addition, due to the ability to fuse two or more than two kinds of hydrophobic polymers, the porous film of the present disclosure has elasticity and flexibility and can be folded and placed in to an endoscopic tube to reach a target position in a surgery, and it can then be spread evenly to perfectly fit a part of the surface of an organ or muscle which is irregularly shaped. Thus it is quite suitable for application in a minimally invasive implantation.

Furthermore, in addition to a tissue-adhesion method, any one porous film mentioned above can be used in a common surgery, to be implanted in a soft tissue to reinforce a frail part of the soft tissue. For example, it can be used in hernia repair; reinforcement of positions which are sutured or nailed; muscle-flap reinforcement; and gastric banding.

In addition, in another aspect of the present disclosure, the use of any porous film of the present disclosure mentioned above for the manufacture of a film used in a tissue-adhesion method is provided.

EXAMPLES

A. Preparation of films

1. Preparation of pure polycaprolactone (PCL) Film (1) 4 g of polycaprolactone (PCL) (Mw. 120K) was added to 10 ml of dichloromethane (DCM), and then mixed with it at 50 rpm for 3 hours to form a polycaprolactone solution.

(2) The polycaprolactone solution mentioned above was poured on a teflon plate, and scraped with a 450 μm scraper to perform a film scraping procedure, and after that, left to stand in a fume hood overnight to form a film.

(3) The film was removed from the teflon plate.

2. Preparation of pure poly(lactic-co-glycolic acid) (PLGA) Film (1) 4 g of poly(lactic-co-glycolic acid)(PLGA) (Mw. 240K) was added to 10 ml of dichloromethane (DCM), and then mixed with it at 50 rpm for 3 hours to form a poly(lactic-co-glycolic acid) solution.

(2) The poly(lactic-co-glycolic acid) solution mentioned above was poured on a teflon plate, and scraped with a 450 μm scraper to perform a film scraping procedure, and after that, left to stand in a fume hood overnight to form a film.

(3) The film was removed from the teflon plate.

3. Preparation of a polycaprolactone/poly(lactic-co-glycolic acid) film of which the manufacturing process uses no salt particles (the weight ratio of polycaprolactone to 240K poly(lactic-co-glycolic acid) Was 4:1)

(1) 3.2±0.05 g of polycaprolactone (PCL, Mw. 120K) was added to 10 ml of dichloromethane (DCM), and then mixed with it at 50 rpm for 3 hours to form a polycaprolactone solution.

(2) 0.8±0.05 g of poly(lactic-co-glycolic acid) (PLGA) (high molecular weight, Mw. 240K) was added to 10 ml of dichloromethane (DCM), and then mixed with it at 50 rpm for 3 hours to form a poly(lactic-co-glycolic acid) solution.

(3) The polycaprolactone solution and the poly(lactic-co-glycolic acid) solution were equal in proportion and mixed to form a mixture solution.

(4) The mixture solution was poured on a teflon plate, and scraped with a 450 μm scraper to perform a film scraping procedure, and after that, left to stand in a fume hood overnight to form a film (the weight ratio of polycaprolactone to poly(lactic-co-glycolic acid) was 4:1).

(5) The film was removed from the teflon plate.

4. Preparation of a polycaprolactone/poly(lactic-co-glycolic acid) film with a process using salt particles (the weight ratio of polycaprolactone to 240K poly(lactic-co-glycolic acid) was 0.25:1)

(1) 0.2±0.05 g of polycaprolactone (PCL, Mw. 120K) was added to 10 ml of dichloromethane (DCM), and then mixed with it at 50 rpm for 3 hours to form a polycaprolactone solution.

(2) 0.8±0.05 g of poly(lactic-co-glycolic acid) (PLGA) (high molecular weight, Mw. 240K) was added to 10 ml of dichloromethane (DCM), and then mixed with it at 50 rpm for 3 hours to form a poly(lactic-co-glycolic acid) solution.

(3) The polycaprolactone solution and the poly(lactic-co-glycolic acid) solution were equal in proportion and mixed to form a mixture solution.

(4) 10±0.05 g of NaCl particles (100-137 mesh (100-140 μm)) were added to the mixture solution of polycaprolactone solution and poly(lactic-co-glycolic acid) solution, stirred clockwise until uniformity was reached to be blended with the polymers, and left to stand for 1-2 minutes to form a solid mixture.

(5) The solid mixture was poured on a teflon plate, and scraped with a 450 μm scraper to perform a film scraping procedure, and after that, left to stand in a fume hood overnight to form a film (the weight ratio of polycaprolactone to poly(lactic-co-glycolic acid) was 0.25:1).

(6) The teflon plate was immersed in a water tank and poked to wash the salt out of the film and make pores form in the film. After that, the film was separated from the teflon plate and carefully and evenly taken out.

5. Preparation of a polycaprolactone/poly(lactic-co-glycolic acid) film with a process using salt particles (the weight ratio of polycaprolactone to 8K poly(lactic-co-glycolic acid) was 4:1)

(1) 3.2±0.05 g of polycaprolactone (PCL, Mw. 120K) was added to 10 ml of dichloromethane (DCM), and then mixed with it at 50 rpm for 3 hours to form a polycaprolactone solution.

(2) 0.8±0.05 g of poly(lactic-co-glycolic acid) (PLGA) (molecular weight, Mw. 8K) was added to 10 ml of dichloromethane (DCM), and then mixed with it at 50 rpm for 3 hours to form a poly(lactic-co-glycolic acid) solution.

(3) The polycaprolactone solution and the poly(lactic-co-glycolic acid) solution were equal in proportion and mixed to form a mixture solution.

(4) 10±0.05 g of NaCl particles (100-137 mesh (100-140 μm)) were added to the mixture solution of polycaprolactone solution and poly(lactic-co-glycolic acid) solution, stirred clockwise until uniformity was reached to be blended with the polymers, and left to stand for 1-2 minutes to form a solid mixture.

(5) The mixture solution was poured on a teflon plate, and scraped with a 450 μm scraper to perform a film scraping procedure, and after that, left to stand in a fume hood overnight to form a film (the weight ratio of polycaprolactone to poly(lactic-co-glycolic acid) solution was 4:1).

(6) The teflon plate was immersed in a water tank and poked to wash the salt out of the film and make pores form in the film. After that, the film was separated from the teflon plate and carefully and evenly taken out.

6. Preparation of a polycaprolactone/poly(lactic-co-glycolic acid) film with a process using salt particles (the weight ratio of polycaprolactone to 240K poly(lactic-co-glycolic acid) was 4:1)

(1) 3.2±0.05 g of polycaprolactone (PCL, Mw. 120K) was added to 10 ml of dichloromethane (DCM), and then mixed with it at 50 rpm for 3 hours to form a polycaprolactone solution.

(2) 0.8±0.05 g of poly(lactic-co-glycolic acid) (PLGA) (high molecular weight, Mw. 240) was added to 10 ml of dichloromethane (DCM), and then mixed with it at 50 rpm for 3 hours to form a poly(lactic-co-glycolic acid) solution.

(3) The polycaprolactone solution and the poly(lactic-co-glycolic acid) solution were equal in proportion and mixed to form a mixture solution.

(4) 10±0.05 g of NaCl particles (100-137 mesh (100-140 μm)) were added to the mixture solution of polycaprolactone solution and poly(lactic-co-glycolic acid) solution, stirred clockwise until uniformity was reached to be blended with the polymers, and left to stand for 1-2 minutes to form a solid mixture.

(5) The solid mixture was poured on a teflon plate, and scraped with a 450 μm scraper to perform a film scraping procedure, and after that, left to stand in a fume hood overnight to form a film (the weight ratio of polycaprolactone to poly(lactic-co-glycolic acid) solution was 4:1).

(6) The teflon plate was immersed in a water tank and poked to wash the salt out of the film and make pores form in the film. After that, the film was separated from the teflon plate and carefully and evenly taken out.

7. Preparation of polycaprolactone/poly(lactic-co-glycolic acid) films with processes using salt particles (in respective processes, the weight ratios of polycaprolactone to 240K poly(lactic-co-glycolic acid) were all 4:1, and the weight ratio of polycaprolactone and 240K poly(lactic-co-glycolic acid) to the salt particles respectively were 1:0.1, 1:2, 1:4, 1:25, 1:100 and 1:200).

(1) 3.2±0.05 g of polycaprolactone (PCL, Mw. 120K) was added to 10 ml of dichloromethane (DCM), and then mixed with it at 50 rpm for 3 hours to form a polycaprolactone solution.

(2) 0.8±0.05 g of poly(lactic-co-glycolic acid) (PLGA) (high molecular weight, Mw. 240) was added to 10 ml of dichloromethane (DCM), and then mixed with it at 50 rpm for 3 hours to form a poly(lactic-co-glycolic acid) solution.

(3) The polycaprolactone solution and the poly(lactic-co-glycolic acid) solution were equal in proportion and mixed to form a mixture solution.

(4) 0.4±0.05 g, 8±0.05 g, 16±0.05 g, 100±0.05 g, 400±0.05 g, or 800±0.05 g of NaCl particles (100-137 mesh (100-140 μm)) were added to the mixture solution of polycaprolactone solution and poly(lactic-co-glycolic acid) solution, stirred clockwise until uniformity was reached to be blended with the polymers, and left to stand for 1-2 minutes to form a solid mixture.

(5) The solid mixture was poured on a plate and scraped from the top downward with a 450 μm scraper at a constant speed to let the solid mixture be capable of coating the plate uniformly.

(6) The plate which was coated with the solid mixture was placed on a shelf for volatilization and left to stand to make the solvent therein volatilize to form a film, and the time for volatilizing was not less than 16 hours.

(7) The plate was immersed in a water tank and poked to wash the salt out of the film and make pores form in the film. After that, the film was separated from the plate and carefully and evenly taken out.

8. Preparation procedure of polycaprolactone/poly(lactic-co-glycolic acid)/drug films with processes using salt particles.

(1) 3.2±0.05 g of polycaprolactone (PCL. Mw. 120K) was added to 10 ml of dichloromethane (DCM), and then mixed with it at 50 rpm for 3 hours to form a polycaprolactone solution.

(2) 0.8±0.05 g of poly(lactic-co-glycolic acid) (PLGA) (high molecular weight, Mw. 240) and 3.2±0.05 g, 1.2±0.05 g, 0.8±0.05 g, 0.4±0.05 g of a hydrophobic drug, citral, (Mw. 153) were added to 10 ml of dichloromethane (DCM), and then mixed with it at 50 rpm for 3 hours to form a drug-mixed poly(lactic-co-glycolic acid) solution.

(3) The polycaprolactone solution and the drug-mixed poly(lactic-co-glycolic acid) solution were equal in proportion and mixed to form a mixture solution. This was able to prepare a mixture solution in which the weight ratio of polycaprolactone to the drug was 1:1, 1:0.375, 1:0.25 or 1:0.125, and wherein the weight ratio of polycaprolactone to poly(lactic-co-glycolic acid) was 4:1.

(4) 16±0.05 g of NaCl particles (100-137 mesh (100-140 μm)) were added to the mixture solution, stirred clockwise until uniformity was reached to be blended with the polymers, and left to stand for 1-2 minutes to form a solid mixture. This was able to prepare a solid mixture in which the weight ratio of polycaprolactone, poly(lactic-co-glycolic acid) and the drug to the NaCl particles was 1:2.2, 1:3.0, 1:3.3 or 1:3.6.

(5) The solid mixture was poured on a plate and scraped from the top downward with a scraper (100-1000 μm) at a constant speed to let the solid mixture be capable of coating the plate uniformly.

(6) The plate which was coated with the solid mixture was placed on a shelf for volatilization and left to stand to make the solvent therein volatilize to form a film, and the time for volatilizing was not less than 16 hours.

(7) The plate was immersed in a water tank and poked to wash the salt out of the film and make pores form in the film. After that, the film was separated from the plate and carefully and evenly taken out.

B. Film Property Analysis

1. Uniformity Analysis for Films

Thermogravimetric Analysis (TGA)

Thermogravimetric analysis is often used to determine the properties of a substance by mass decrease or increase resulting from decomposition, oxidation or volatilization (such as volatilization of moisture content). Thermogravimetric analysis can be used to accurately predict material structure, or it can be directly used as a chemical analysis, and as a technique for observing blending uniformity.

A thermogravimetric analyzer used in the present experiment was Pyris 1 TGA. The procedure for operation and analysis is described in the following paragraphs.

The machine and computer were turned on, and it was confirmed that the machine was connected to the computer. The gas used was high-purity nitrogen, and it was confirmed that the nitrogen was sufficient and was led into the machine. "Pyris Manager" was clicked, and the thermogravimetric analysis software was started. The determining parameter conditions were set: Initial temperature was 25° C. The temperature was increased to 700° C. at a rate of 20° C. per minute and maintained at 700° C. for 15 minutes. Information related to the file was filled out, such as storage location, file name, remarks, etc. According to the operation of the machine, a required platinum plate was hung on a balance of the machine, a button for balancing was clicked to reset the weight of the platinum plate to zero. A temperature controlling barrier was lowered and the platinum plate was taken out and a sample to be tested was placed on the platinum plate, and the weight of the sample was controlled at 3-30 mg. A button for weighting was clicked to weigh the sample, and after the weight was determined, the measurement was begun. The result of the measurement was saved as an ASC file and analyzed.

First, the influence of a content of polycaprolactone and the molecular weight of poly(lactic-co-glycolic acid) on the uniformity of a polycaprolactone/poly(lactic-co-glycolic acid) film was determined to obtain an appropriate proportion for uniformly blending.

Films formed by blending different weights of polycaprolactone to a fixed weight of poly(lactic-co-glycolic acid) with different molecular weight ((A) the molecular weight of poly(lactic-co-glycolic acid) was 240K, and the ratio of polycaprolactone to poly(lactic-co-glycolic acid) was 0.25:1; (B) the molecular weight of poly(lactic-co-glycolic acid) was 8K, and the ratio of polycaprolactone to poly(lactic-co-glycolic acid) was 4:1; (C) the molecular weight of poly(lactic-co-glycolic acid) was 240K, and the ratio of polycaprolactone to poly(lactic-co-glycolic acid) was 4:1), were observed for composition uniformity at different locations (a film was cross cut into three sections: an upper section, a middle section, and a lower section) using a thermogravimetric analyzer. The results are shown in FIGS. 1A-1C.

Figure 1B:
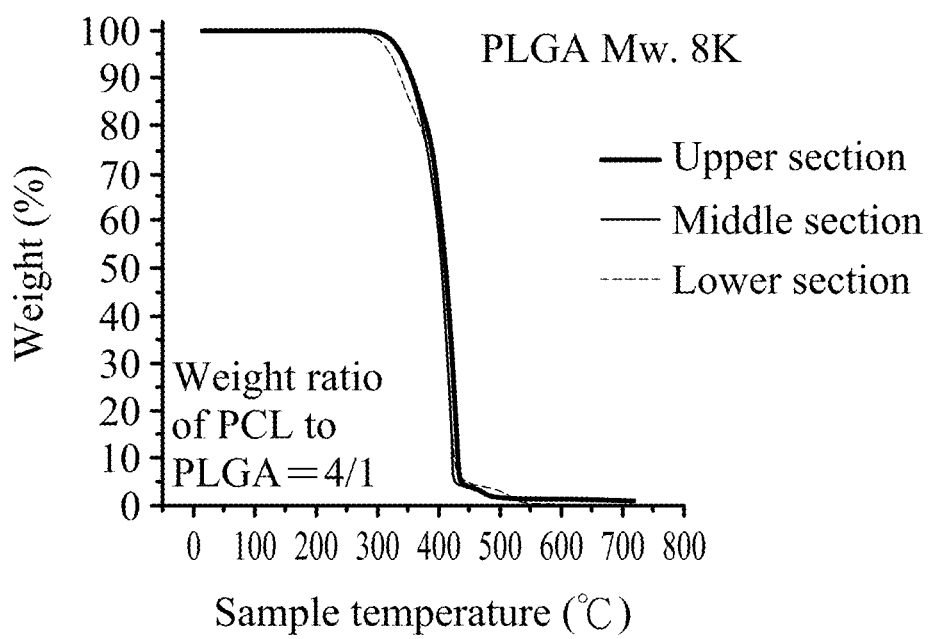
FIG. 1B shows thermogravimetric analysis results of the film prepared by a process in which the molecular weight of the poly(lactic-co-glycolic acid) is 8K, and the weight ratio of the polycaprolactone to the poly(lactic-co-glycolic acid) is 4:1, at different locations.
Figure 1C:
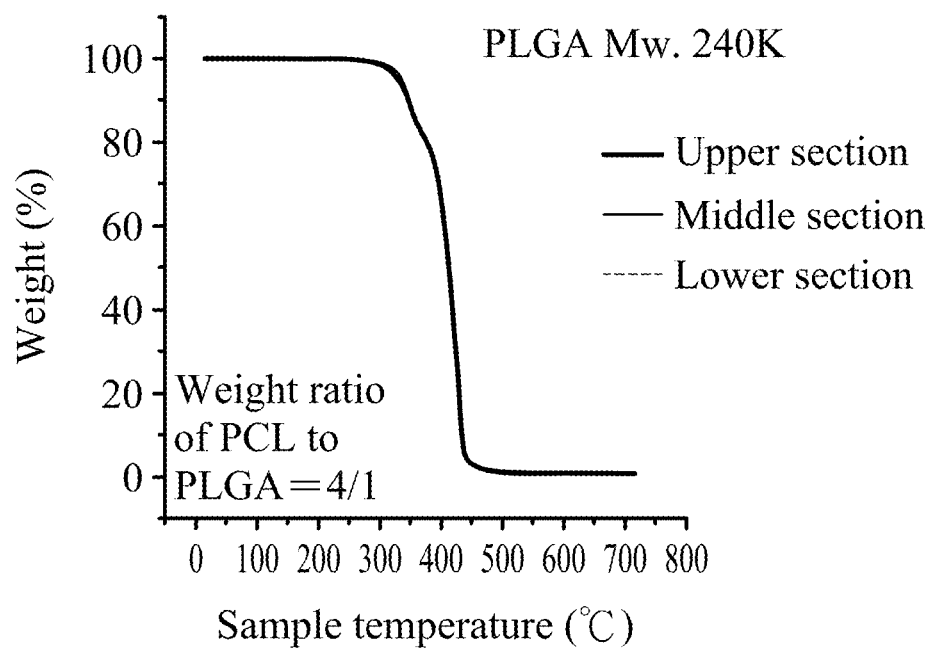
FIG. 1C shows thermogravimetric analysis results of the film prepared by a process in which the molecular weight of the poly(lactic-co-glycolic acid) is 240K, and the weight ratio of the polycaprolactone to the poly(lactic-co-glycolic acid) is 4:1, at different locations.
Figure 2A:
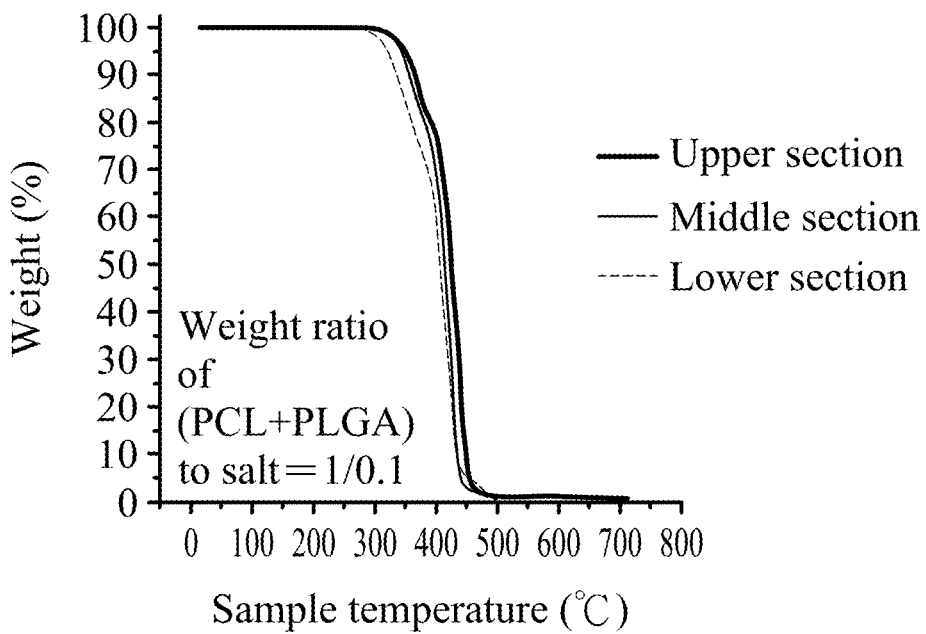
FIG. 2A shows thermogravimetric analysis results of a polycaprolactone/poly(lactic-co-glycolic acid) film prepared by a process of the present disclosure in which the molecular weight of the poly(lactic-co-glycolic acid) is 240K, the weight ratio of the polycaprolactone to the poly(lactic-co-glycolic acid) is 4:1, and the weight ratio of the polycaprolactone and the poly(lactic-co-glycolic acid) to the salt particles is 1:0.1, at different locations.
Figure 2B:
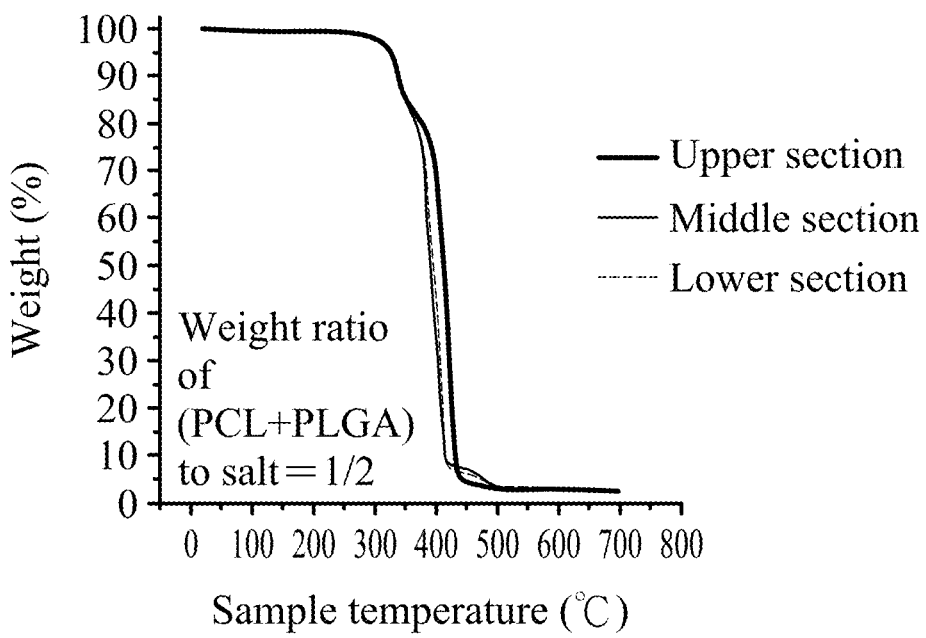
FIG. 2B shows thermogravimetric analysis results of a polycaprolactone/poly(lactic-co-glycolic acid) film prepared by a process of the present disclosure in which the molecular weight of the poly(lactic-co-glycolic acid) is 240K, the weight ratio of the polycaprolactone to the poly(lactic-co-glycolic acid) is 4:1, and the weight ratio of the polycaprolactone and the poly(lactic-co-glycolic acid) to the salt particles is 1:2, at different locations.
Figure 2C:
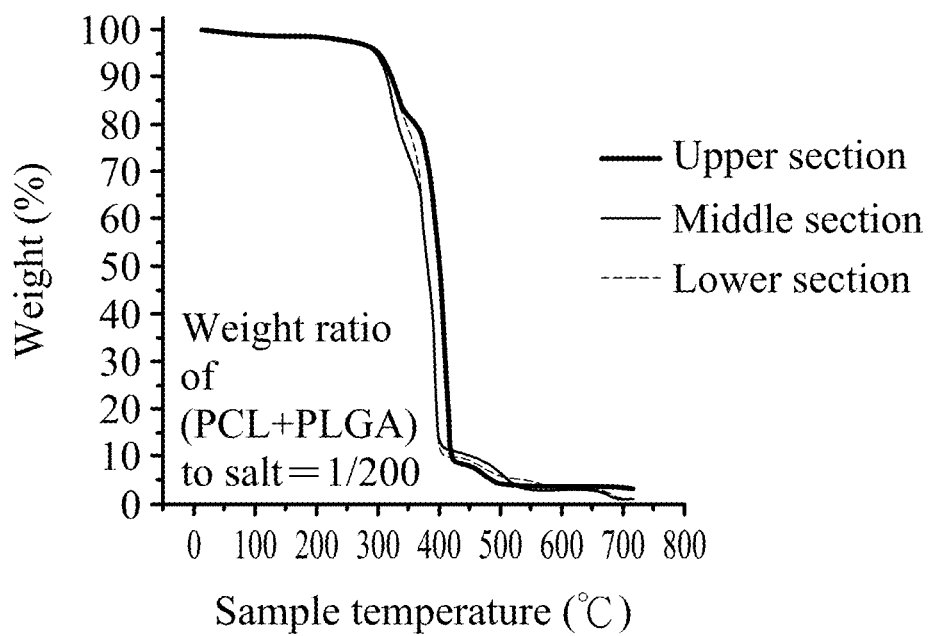
FIG. 2C shows thermogravimetric analysis results of a polycaprolactone/poly(lactic-co-glycolic acid) film prepared by a process of the present disclosure in which the molecular weight of the poly(lactic-co-glycolic acid) is 240K, the weight ratio of the polycaprolactone to the poly(lactic-co-glycolic acid) is 4:1, and the weight ratio of the polycaprolactone and the poly(lactic-co-glycolic acid) to the salt particles is 1:200, at different locations.
Figure 2D:
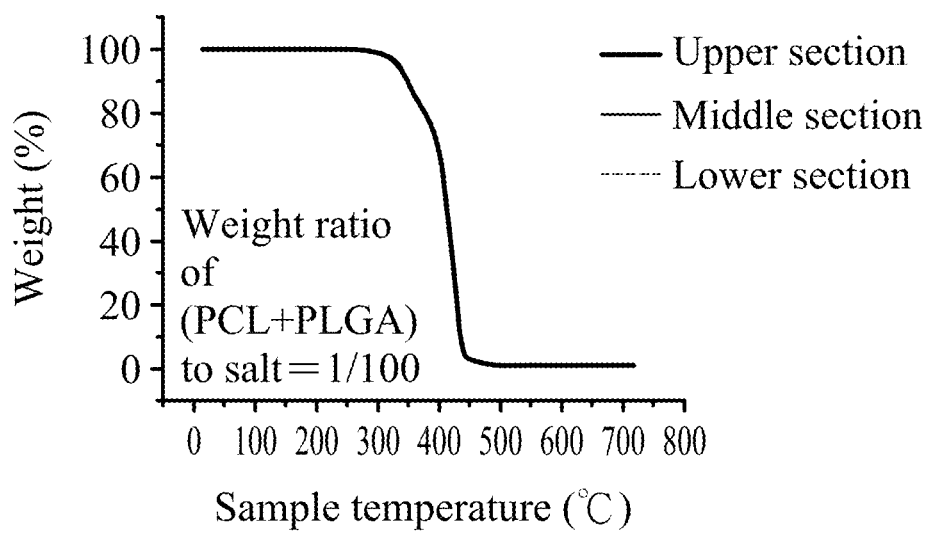
FIG. 2D shows thermogravimetric analysis results of a polycaprolactone/poly(lactic-co-glycolic acid) film prepared by a process of the present disclosure in which the molecular weight of the poly(lactic-co-glycolic acid) is 240K, the weight ratio of the polycaprolactone to the poly(lactic-co-glycolic acid) is 4:1, and the weight ratio of the polycaprolactone and the poly(lactic-co-glycolic acid) to the salt particles is 1:100, at different locations.

FIGS. 1A-1C shows that when poly(lactic-co-glycolic acid) has a specific molecular weight, and polycaprolactone and poly(lactic-co-glycolic acid) are at a specific proportion (the molecular weight of the poly(lactic-co-glycolic acid) is 240K, and a weight ratio of polycaprolactone to poly(lactic-co-glycolic acid) is 4:1), uniform blending can be reached, the TGA curves can completely overlap without phase separation occurring (see FIG. 1C).

Next, the influence of adding different proportions of salt solid particles to blend with polycaprolactone and poly(lactic-co-glycolic acid) in a film manufacturing process on the uniformity of a polycaprolactone/poly(lactic-co-glycolic acid) film was determined.

Films were formed by film processes in which different weights of salt particles were used for blending, were observed for composition uniformity at different locations (a film was cross cut into three sections: an upper section, a middle section, and a lower section) using a thermogravimetric analyzer. The results are shown in FIGS. 2A-2D.

FIGS. 2A-2D show that, for the salt particles, when the weight ratio of polycaprolactone and poly(lactic-co-glycolic acid) to the salt particles is 1:100, a film was most uniformly formed.

Then, the influence of adding salt solid particles or not to blend with polycaprolactone and poly(lactic-co-glycolic acid) in a film manufacturing process on the uniformity of a polycaprolactone/poly(lactic-co-glycolic acid) film was determined.

A pure polycaprolactone film, a pure poly(lactic-co-glycolic acid) film, a polycaprolactone/poly(lactic-co-glycolic acid) film of which the manufacturing process added salt solids (the weight ratio of polycaprolactone to 240K poly(lactic-co-glycolic acid) was 4:1, the weight ratio of polycaprolactone and poly(lactic-co-glycolic acid) to the salt particles was 1:100), and a polycaprolactone/poly(lactic-co-glycolic acid) film of which the manufacturing process added no salt solids (the weight ratio of polycaprolactone to 240K poly(lactic-co-glycolic acid) was 4:1), were observed for composition uniformity at different locations using a thermogravimetric analyzer, wherein the polycaprolactone/poly(lactic-co-glycolic acid) film of which the manufacturing process added salt solids, and the polycaprolactone/poly(lactic-co-glycolic acid) film of which the manufacturing process added no salt solids were cross cut into three sections: an upper section, a middle section, and a lower section. The results are shown in FIGS. 3A and 3B.

Figure 3A:
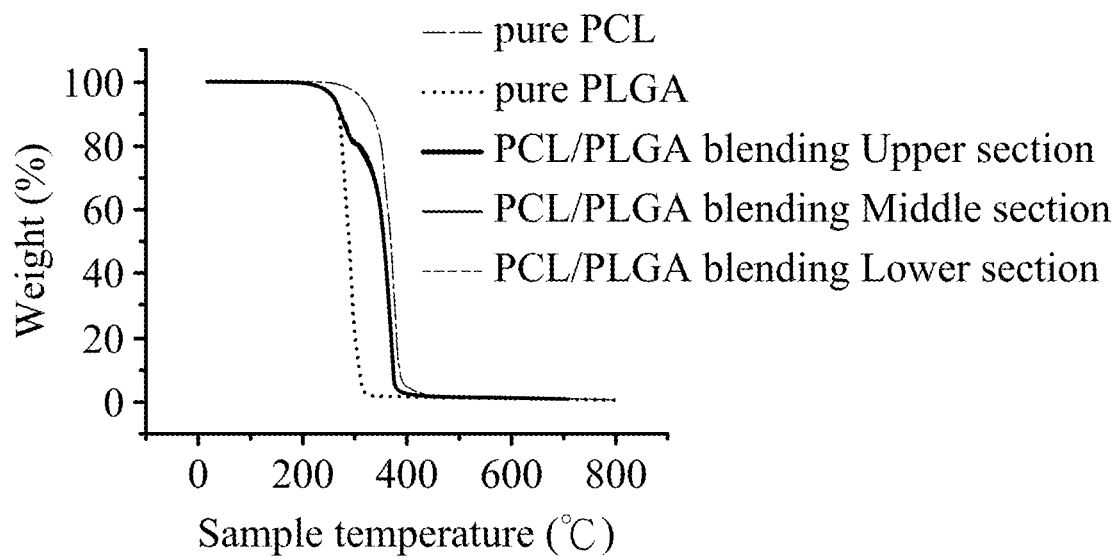
FIG. 3A shows thermogravimetric analysis results of a pure polycaprolactone film, a pure poly(lactic-co-glycolic acid) film, a polycaprolactone/poly(lactic-co-glycolic acid) film prepared by a process in which salt solids are added (the weight ratio of the polycaprolactone to 240K poly(lactic-co-glycolic acid) is 4:1, the weight ratio of the polycaprolactone and poly(lactic-co-glycolic acid) to the salt particles is 2:0.05)

FIG. 3A shows the thermogravimetric analysis results for the pure polycaprolactone film, the pure poly(lactic-co-glycolic acid) film, and the polycaprolactone/poly(lactic-co-glycolic acid) film of which the manufacturing process added salt solids (the weight ratio of polycaprolactone to 240K poly(lactic-co-glycolic acid) was 4:1, the weight ratio of polycaprolactone and poly(lactic-co-glycolic acid) to the salt particles was 1:100). FIG. 3B shows the thermogravimetric analysis results for the pure polycaprolactone film, the pure poly(lactic-co-glycolic acid) film, and the polycaprolactone/poly(lactic-co-glycolic acid) film of which the manufacturing process added no salt solids (the weight ratio of polycaprolactone to 240K poly(lactic-co-glycolic acid) was 4:1).

Figure 3B:
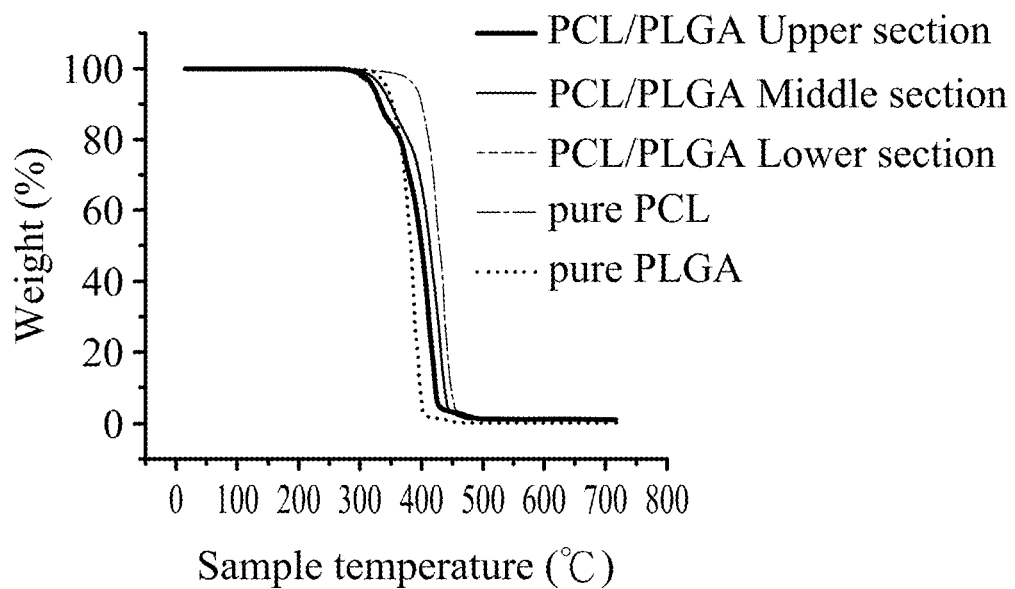
FIG. 3B shows thermogravimetric analysis results of a pure polycaprolactone film, a pure poly(lactic-co-glycolic acid) film, a polycaprolactone/poly(lactic-co-glycolic acid) film in which the weight ratio of the polycaprolactone to poly(lactic-co-glycolic acid) is 4:1.

According to FIGS. 3A and 3B, adding a specific proportion of solid particles during the manufacturing of a film (the process of the present disclosure) lets the polycaprolactone blend uniformly with poly(lactic-co-glycolic acid) without phase separation occurring, while a film formed without using the process of the present disclosure (a polycaprolactone/poly(lactic-co-glycolic acid) prepared by a process without adding salt solids) is extremely nonuniform.

Then, thermogravimetric analyses were performed on polycaprolactone/poly(lactic-co-glycolic acid)/drug films of which the manufacturing process used salt particles.

Figure 4:
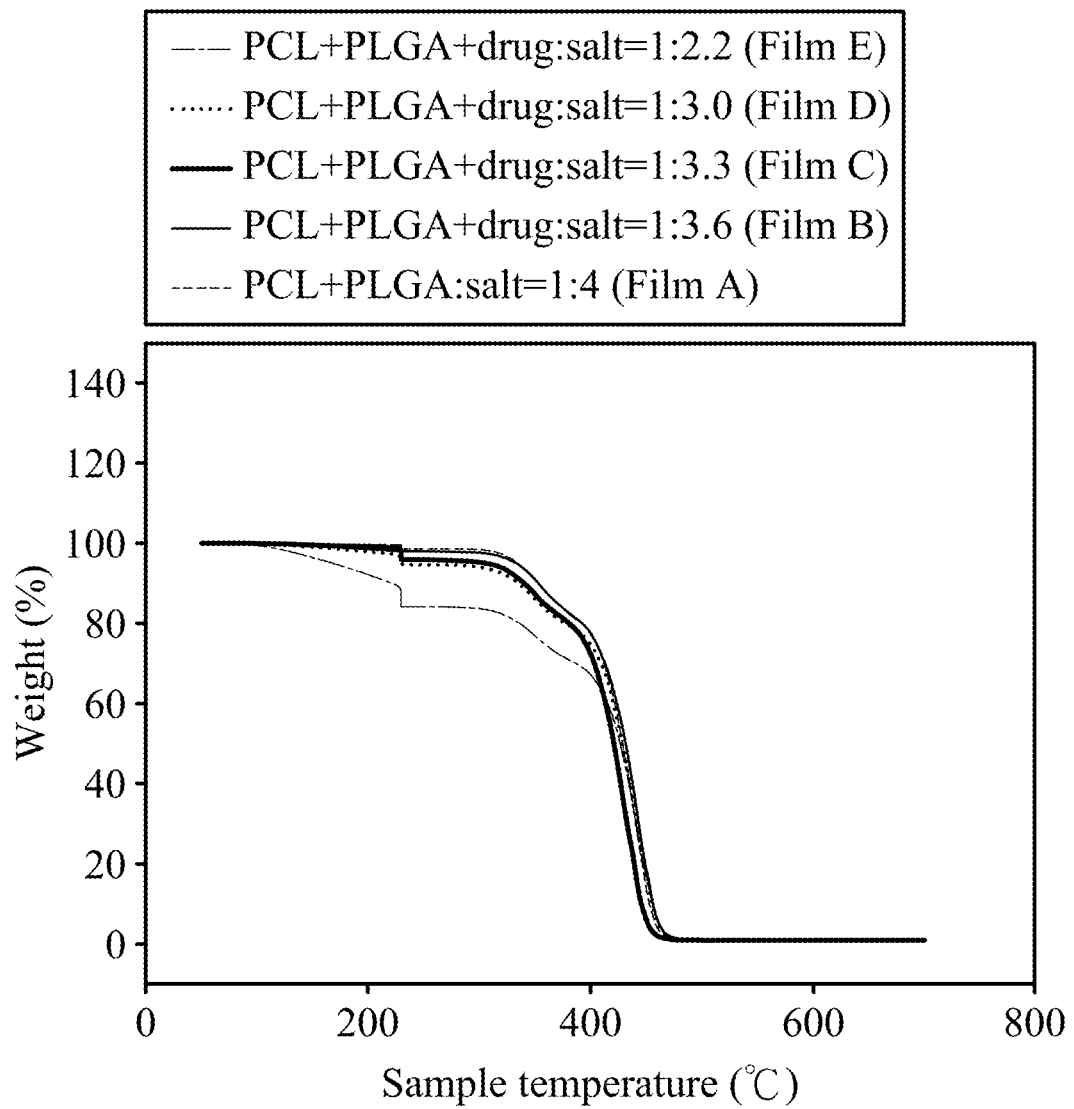
FIG. 4 shows thermogravimetric analysis results of various polycaprolactone/poly(lactic-co-glycolic acid)/drug films prepared by processes in which salt particles are used.

Thermogravimetric analyses were performed on the polycaprolactone/poly(lactic-co-glycolic acid) film A (the weight ratios of polycaprolactone and poly(lactic-co-glycolic acid) to the salt particles were all 1:2.5) of which the manufacturing process used salt particles, and the polycaprolactone/poly(lactic-co-glycolic acid)/drug films B-E of which the manufacturing process used salt particles (for the films, the weight ratios of polycaprolactone and poly(lactic-co-glycolic acid) to the salt particles were all 1:2.5, and the weight ratios of polycaprolactone to 240K PLGA to the drug were 4:1:0.5, 4:1:1, 4:1:1.5 and 4:1:4, respectively), and the results are shown in FIG. 4.

According to FIG. 4, it is known that when the weight ratio of polycaprolactone, poly(lactic-co-glycolic acid) and the drug to solid particles is within the range of 1:2-100, a film can be formed.

Furthermore, based on the weight at a temperature of 210° C. lower than the boiling point of citral (229° C.) and the weight at a temperature of 240° C. higher than the boiling point of citral which were obtained by the thermogravimetric analyses, weight loss for each film was calculated, and this weight loss is due to citral evaporation at its boiling point. Therefore, encapsulation efficiency of each film to citral (the actual citral content for each film) can be known. The results are shown in Table 1.

TABLE 1

| Film code | A | B | C | D | E |
|---|---|---|---|---|---|
| PCL:PLGA:citral | 4:1:0 | 4:1:0.5 | 4:1:1 | 4:1:1.5 | 4:1:4 |
| PCL + PLGA + citral:salt | 1:4[a] | 1:3.6 | 1:3.3 | 1:3.0 | 1:2.2 |
| Weight at 210° C. | 99.9% | 99.8% | 98.7% | 97.8% | 92.4% |
| Weight at 240° C. | 99.6% | 97.1% | 94.9% | 94.5% | 84.1% |
| Weight loss (citral) | 0.3% | 2.7% | 3.8% | 3.3% | 8.3% |
| Expected encapsulation amount | 0% | 9.0% | 16% | 23 | 44% |
| Theoretical density (g/cm$^3$) | 1.166 | 1.141 | 1.120 | 1.103 | 1.044 |

[a]This ratio was a ratio of (PCL + PLGA):salt

Based on Table 1, it is known that encapsulation efficiencies of polycaprolactone/poly(lactic-co-glycolic acid)/drug films prepared by the examples of the present disclosure to citral are about 2-10%.

2. Tensile Tests

Tensile tests were performed on a pure polycaprolactone film and a polycaprolactone/poly(lactic-co-glycolic acid) film of which the manufacturing process added salt solids (the weight ratio of polycaprolactone to 240K poly(lactic-co-glycolic acid) was 4:1, and the weight ratio of polycaprolactone and poly(lactic-co-glycolic acid) to the salt particles was 1:100) according to Standard Test Method for Tensile Properties of Thin Plastic Sheeting defined by ASTM D882-12.

ASTM D882-12 standard is used to determine tensile properties, especially suitable for a plastic film with a thickness of less than 1 mm. Base on this standard, a test specimen was cut using a sharp cutter to a strip of 100*25.4 mm$^2$, and the initial distance between the upper and lower pneumatic chucks were adjusted to 100 mm, and the pulling speed was set to 50 mm/minute. The test results are shown in FIG. 5.

Figure 5:
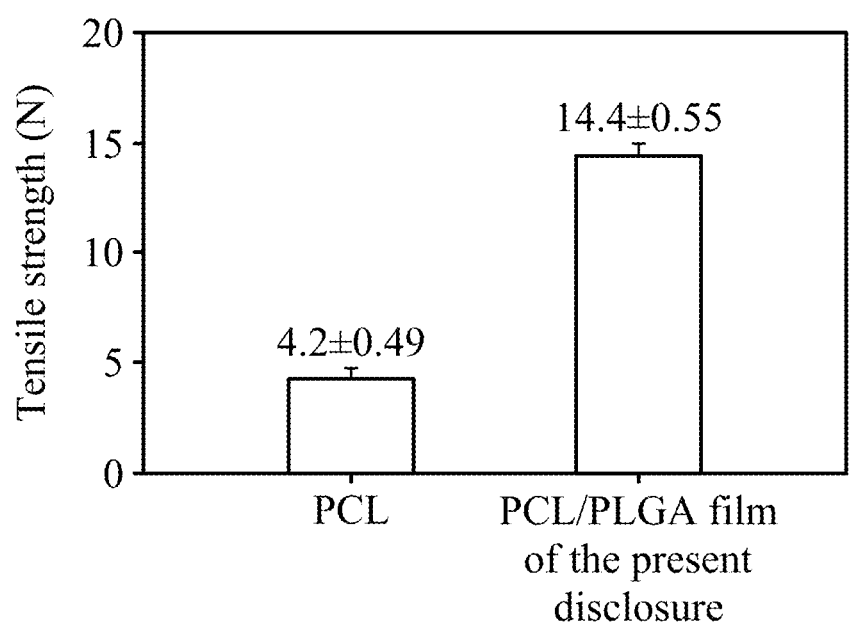
FIG. 5 shows the results of a standard test of tensile properties for a pure polycaprolactone film and a film prepared by the process of the disclosure (the weight ratio of the polycaprolactone to 240K poly(lactic-co-glycolic acid) is 4:1, and the weight ratio of the polycaprolactone and the poly(lactic-co-glycolic acid) to the salt particles is 1:100)

The results are shown in FIG. 5. The polycaprolactone/poly(lactic-co-glycolic acid) film of which the manufacturing process added salt solids combines physicochemical properties of polycaprolactone and poly(lactic-co-glycolic acid). Tensile strength of the pure polycaprolactone film without blending with poly(lactic-co-glycolic acid) was only about 4-5 N, while after being blended with poly(lactic-co-glycolic acid) through the process of the present disclosure, tensile strength of the film could be increased to about 10.2-15 N.

3. Surface Structure and Roughness of Films (1) Observation of Surface Structure Surface micro structure for a film of the present disclosure was analyzed by environmental scanning electron microscopy (ESEM). The catalog number of the environmental scanning electron microscope was JEOL JSM-5610LV. The film was cut to a sample of 0.5×0.5 cm$^2$, and the sample was attached on a sample stage configured by the environmental scanning electron microscope by carbon tape. After that, a gold-plating treatment was performed on the stage along with the sample, and the time for gold-plating was about 90 seconds. After gold-plating was completed, the stage was placed into the ESEM. After that, vacuum was created, the software was started and conditions required by the analysis were set: Vacuum Mode was set as HV mode, Depth of field for electron beam (WD) was set to 10 mm, Voltage for electron beam was set to 5 kV, and magnification factor was adjusted and between 35× and 1000×, and analysis was performed. Roughness for the micro structure of the sample surface could be observed. After the capture of the needed magnifying screens was completed, and the file was saved, the electron beam was turned off. After vacuum relief was performed on the ESEM, the sample was taken out and the analysis of the surface micro structure was completed.

Figure 6A:
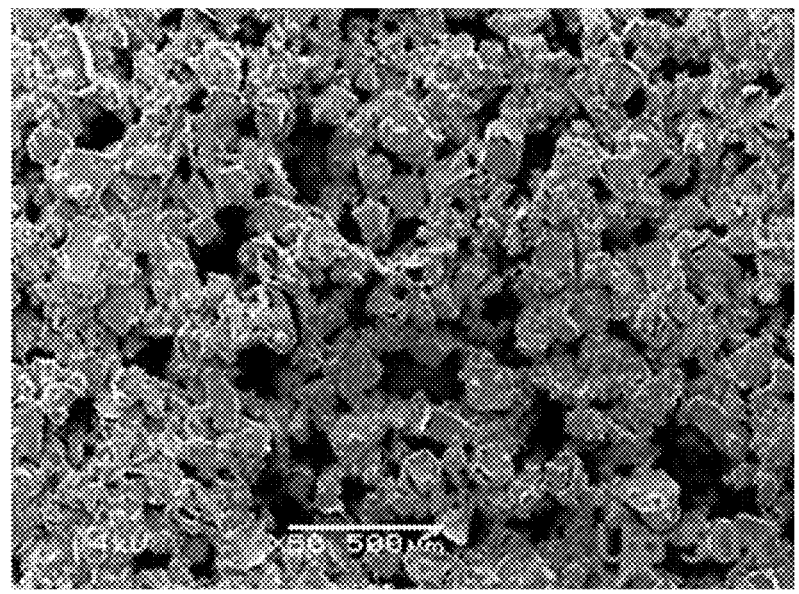
FIG. 6A shows an environmental scanning electron microscopy photograph of the top surface of a film prepared by the process of the disclosure (the weight ratio of the polycaprolactone to 240K poly(lactic-co-glycolic acid) is 4:1, and the weight ratio of the polycaprolactone and the poly(lactic-co-glycolic acid) to the salt particles is 1:2.5)
Figure 6B:
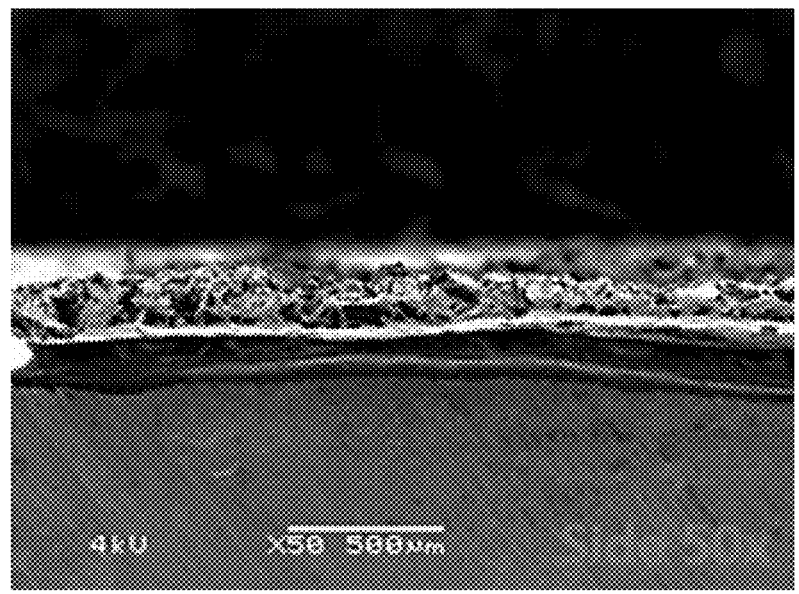
FIG. 6B shows an environmental scanning electron microscopy photograph of the side face of a film prepared by the process of the disclosure (the weight ratio of the polycaprolactone to 240K poly(lactic-co-glycolic acid) is 4:1, and the weight ratio of the polycaprolactone and the poly (lactic-co-glycolic acid) to the salt particles is 1:2.5)
Figure 6C:
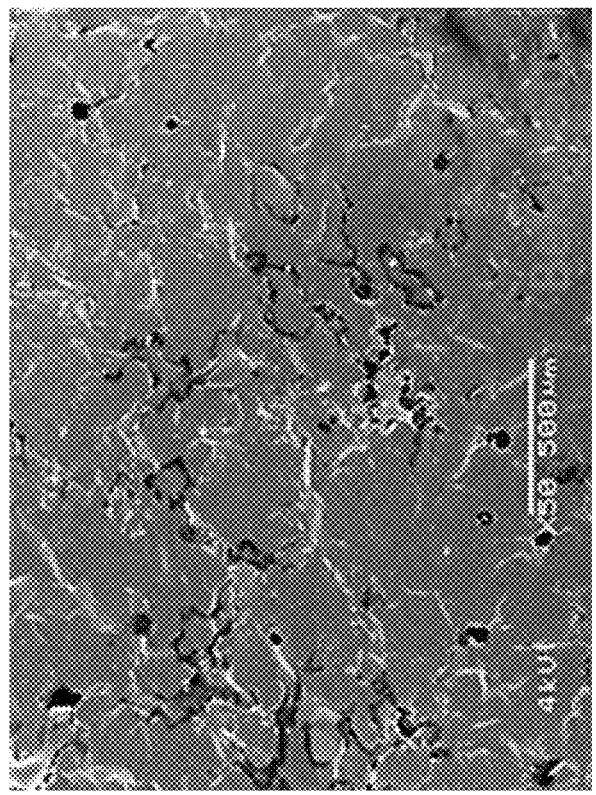
FIG. 6C shows an environmental scanning electron microscopy photograph of the bottom surface of a film prepared by the process of the disclosure (the weight ratio of the polycaprolactone to 240K poly(lactic-co-glycolic acid) is 4:1, and the weight ratio of the polycaprolactone and the poly(lactic-co-glycolic acid) to the salt particles is 1:2.5)

Surface structure observation was performed on a polycaprolactone/poly(lactic-co-glycolic acid) film of which the manufacturing process added salt solids (the weight ratio of polycaprolactone to 240K poly(lactic-co-glycolic acid) was 4:1, and the weight ratio of polycaprolactone and poly(lactic-co-glycolic acid) to the salt particles was 1:2.5) (a film prepared by the process of the present disclosure) by the environmental scanning electron microscopy mentioned above. FIG. 6A shows an environmental scanning electron microscopy photograph of the top surface of the film prepared by the process of the disclosure. FIG. 6B shows an environmental scanning electron microscopy photograph of the side face of the film prepared by the process of the disclosure. FIG. 6C shows an environmental scanning electron microscopy photograph of the bottom surface of a film prepared by the process of the disclosure.

The results show that for the film prepared by the process of the present disclosure, the thickness of the film was about 100 μm, porosity was >80%, pore size was about 72±16.9 μm, and the two surfaces of the film had different structures.

For the film prepared by the process of the present disclosure, the top surface thereof has high roughness while the bottom surface thereof was a smooth structure. The top surface with high roughness has higher friction to injured tissue and is easy to be fixed thereon. In contrast, the bottom surface which is a smooth structure is capable of easily attaching to a mucosa or fascia. The film prepared by the process of the present disclosure due to the different structures of the two surfaces, is capable of accelerating adhesion for different tissues.

Moreover, the film prepared by the process of the present disclosure with different roughnesses of the two surfaces only has a thickness of 100 μm, and is very convenient for use in minimally invasive surgery, and the interior of the film can assist tissue metabolism and nutrient transfer due to its high porosity.

(2) Roughness

Roughness determinations were performed on polycaprolactone/poly(lactic-co-glycolic acid) films of which the manufacturing processes added salt solids with different sizes and polycaprolactone/poly(lactic-co-glycolic acid) films of which the manufacturing processes added different proportions of salt solids, according to Standard Test Method for Surface Roughness defined by ASTM D7127-13.

Measurement was performed according to ASTM D7127-13 standard. The measuring instrument used was Surfcorder SE1700. The principle behind this measurement is that, by scanning the height difference of a test specimen with a probe through a light reflection and using scattering transmission, the reflective signals from the light sources which are on and under the probe were converted and calculated to draw a sectional drawing to determine the film thickness variation and surface roughness. After that, full roughness (Rz) was calculated.

Calculation of full roughness (Rz) is summarized in the following paragraph.

An estimated length was divided equally into 5 aliquots of a sample length, and the distance between the highest point and the lowest point in each aliquot of the sample length was calculated, and then all the distances between the highest point and the lowest point in each aliquot of the sample length are summarized and averaged to obtain the full roughness.

Formula for full roughness is shown in the following:

$$Rz = \frac{R_{y1} + R_{y2} + R_{y3} + R_{y4} + R_{y5}}{5}$$

wherein $R_{y1}$, $R_{y2}$, $R_{y3}$, $R_{y4}$ and $R_{y5}$ respectively represent the distance between the highest point and the lowest point in the first aliquot to the fifth aliquot.

The results are shown in Table 2 and Table 3. Table 2 shows the full roughness of the polycaprolactone/poly(lactic-co-glycolic acid) films of which the manufacturing processes adds salt solids of different sizes, and Table 3 shows the full roughness of the polycaprolactone/poly(lactic-co-glycolic acid) films of which the manufacturing processes adds different proportions of salt solids.

TABLE 2

Full roughness of the polycaprolactone/poly(lactic-co-glycolic acid) films of which the manufacturing processes adds salt solids with different sizes

| Particle size of salt | >150 μm | 100-140 μm | <90 μm |
|---|---|---|---|
| Weight ratio of PCL + PLGA to salt | 1:4 | 1:4 | 1:4 |
| Full roughness (Rz) | 85.63 ± 8.222 μm | 95.09 ± 10.197 μm | 90.75 ± 15.584 μm |

TABLE 3

Full roughness of the polycaprolactonelpoly(lactic-co-glycolic acid) films of which the manufacturing processes adds different proportions of salt solids

| Particle size of salt | 100-140 μm | 100-140 μm | 100-140 μm |
|---|---|---|---|
| Weight ratio of PCL + PLGA to salt | 1:2.5 | 1:4 | 1:25 |
| Full roughness (Rz) | 118.5 ± 3.85 μm | 95.09 ± 10.197 μm | 79.83 ± 4.427 μm |

The results show that the particle size of the salt particles did not influence the roughness of the film surface (Table 2), however, the weight ratio of the polymers to the salt particles influenced the roughness of the film surface (Table 3). Therefore, in the process of the present disclosure, the roughness of the film surface can be controlled by the weight ratio of the polymers to the salt particles.

4. Tests for Density and Porosity

Determinations for the weight and thickness of films were performed on the polycaprolactone/poly(lactic-co-glycolic acid) film A of which the manufacturing process added salt solids (the weight ratios of polycaprolactone and poly(lactic-co-glycolic acid) to the salt particles were all 1:2.5, and the weight ratio of polycaprolactone to 240K PLGA was 4:1), and the polycaprolactone/poly(lactic-co-glycolic acid)/drug films B-E of which the manufacturing process used salt particles (for the films, the weight ratios of polycaprolactone and poly(lactic-co-glycolic acid) to the salt particles were all 1:2.5, and the weight ratios of polycaprolactone to 240K PLGA to the drug were 4:1:0.5, 4:1:1, 4:1:1.5 and 4:1:4, respectively) according to Standard Guide for Characterization and Testing of Biomaterial Scaffolds Used in Tissue-Engineered Medical Products defined by ASTM F2150-02 and Standard Test Method of Apparent Density of Rigid Cellular Plastics defined by ASTM D1622-08, through the basic relation between weight and volume.

TABLE 4

Thickness of films

| Determining position | Film A | Film B | Film C | Film D | Film E |
|---|---|---|---|---|---|
| Upper left | 0.131 | 0.167 | 0.139 | 0.160 | 0.166 |
| Upper | 0.129 | 0.167 | 0.143 | 0.175 | 0.176 |
| Upper right | 0.138 | 0.152 | 0.144 | 0.182 | 0.159 |
| Left | 0.128 | 0.159 | 0.149 | 0.177 | 0.169 |
| Middle | 0.137 | 0.148 | 0.161 | 0.172 | 0.168 |
| Right | 0,139 | 0.154 | 0.148 | 0.167 | 0.181 |
| Lower left | 0.141 | 0.159 | 0.149 | 0.168 | 0.174 |

TABLE 4-continued

Thickness of films

| Determining position | Film A | Film B | Film C | Film D | Film E |
|---|---|---|---|---|---|
| Lower | 0.153 | 0.163 | 0.159 | 0.184 | 0.168 |
| Lower right | 0.151 | 0.153 | 0.161 | 0.170 | 0.179 |
| Average thickness ± standard deviation (mm) (Mean/standard deviation %) | 0.139 ± 0.0088 (6.3%) | 0.158 ± 0.0067 (4.2%) | 0.150 ± 0.0015 (1.0%) | 0.173 ± 0.0038 (2.1%) | 0.171 ± 0.0032 (1.8%) |

A film (15 cm×15 cm) was taken out and the middle part of 12 cm×12 cm thereof was taken, and then divided into four pieces of film with a size of 6 cm-6 cm. The volume of the film can be known by determining the thickness of the film, and the actual density can be inferred by the volume and the weight. The porosity of a film can be obtained by the following formula.

Formula of porosity:

$$\text{Porosity}(P)\% = 1 - \rho/\rho_{th},$$

wherein $\rho$ is actual density, and $\rho_{th}$ is theoretical density.

86 The theoretical density of PCL material is 1.145 g/cm$^3$; the theoretical density of PLGA material is 1.25 g/cm$^3$; the theoretical density of citral material is 0.893 g/cm$^3$. The calculation formula for theoretical density for each film is shown in the following: [(Weight of PCL*1.145+Weight of PLGA*1.25+Weight of citral*0.893)/Weight of PCL+PLGA+citral]×Film thickness (cm) (average film thickness shown in Table 4)

Calculation formula for real density for each film is shown in the following: (Weight/Volume)×Film thickness (cm) (average film thickness shown in Table 4)

The porosity for each film is shown in Table 5.

TABLE 5

| Film code | Weight (g) | Volume (cm$^3$) | Actual density (g/cm$^2$) | Theoretical density (g/cm$^2$) | Porosity (%) |
|---|---|---|---|---|---|
| Film A | 0.06477 | 0.34639 | 2.5 * 10$^{-3}$ | 1.6 * 10$^{-2}$ | 83.9% |
| Film B | 0.06829 | 0.39500 | 2.7 * 10$^{-3}$ | 1.8 * 10$^{-2}$ | 84.8% |
| Film C | 0.07329 | 0.37583 | 2.9 * 10$^{-3}$ | 1.6 * 10$^{-2}$ | 82.5% |
| Film D | 0.07761 | 0.43194 | 3.1 * 10$^{-3}$ | 1.9 * 10$^{-2}$ | 83.9% |
| Film E | 0.08270 | 0.4277 | 3.3 * 10$^{-3}$ | 1.7 * 10$^{-2}$ | 81.4% |

The density of the films prepared in the examples of the present disclosure was 2.0-5.0×10$^{-3}$ g/cm$^2$ (the average thickness of the films was 0.12-0.19 cm), and that was far less than the highest density (>25 g/cm$^2$) of most commercial surgical mesh (Vicryl Woven Mesh). The average porosity of the films prepared by the process of the present disclosure was between 81% and 85%, and for the same film, the standard deviation for the results which were determined at different locations was less than 0.5%, and this indicated that the films prepared by the process of the present disclosure had high porosity, and the porous structures were uniformly distributed. The literature indicates that a biodegradable mesh which is lighter and has high porosity has a better effect on tissue compliance and repair, and does not induce serious tissue inflammation as easily.

5. Animal Experiments (1) Pleurodesis of Pigs in Large Animal Experiments (a) Surgery Procedure for the Control Group (Physical Rub):

For animal feeding, before a surgery, the animal was subjected to adaptation for at least one week. Overnight fasting was performed to the animal.

Anesthesia was administered to the experimental pig (injection at the neck). After that, a drainage needle tube was set up at an ear of the pig to boost Citosol depending on the anesthetic condition of the pig during the surgery.

The location to be subjected to surgery was washed (left chest), and then hairs thereon were sheared, and the iodine was sprayed thereon.

A location near the left scapula was cut using a scalpel (a local anesthetic was previously injected) to make a long and deep wound, and after that, the wound was reamed by a hemostat and a scalpel and undermined to the chest wall and a breach was made at the chest wall.

Blood at the wound was absorbed and removed to increase visibility of the surgery, and then an endoscope was inserted into the chest so that the lung and the beating heart under the lung could be observed.

After a position was determined by the endoscope, gauze was folded and nipped and then placed on the upper brim of the lung to rub the parietal pleura at the upper brim (rubbing area was about 10×10 cm$^2$).

After the rubbing was completed, the air in the pleural space was sucked out, and then the related instruments were taken out and the wound was sutured.

(b) Surgery Procedure for the Experimental Group (Implantation of the Film of the Present Disclosure)

For animal feeding, before a surgery, the animal was subjected to adaptation for at least one week. Overnight fasting was performed to the animal.

Anesthesia was administered to the experimental pig (injection at the neck). After that, a drainage needle tube was set up at an ear of the pig to boost Citosol depending on the anesthetic condition of the pig during the surgery.

The location to be subjected to surgery was washed (left chest), and then hairs thereon were sheared, and the iodine was sprayed thereon.

A location near the left scapula was cut using a scalpel (a local anesthetic was previously injected) to make a long and deep wound, and after that, the wound was reamed by a hemostat and a scalpel and undermined to the chest wall and a breach was made at the chest wall.

Blood at the wound was absorbed and removed to increase visibility of the surgery, and then an endoscope was inserted into the chest so that the lung and the beating heart under the lung could be observed.

After a position was determined by the endoscope, a film of the present disclosure (in the process, the weight ratio of polycaprolactone to 240K poly(lactic-co-glycolic acid) was 4:1, and the weight ratio of polycaprolactone and poly (lactic-co-glycolic acid) to the salt particles was 1:100) was folded and nipped and then evenly spread on the upper brim of the lung.

After the placement, the air in the pleural space was sucked out, and then the related instruments were taken out and the wound was sutured.

Table 6 shows the manners of operation for the experimental group and the control group.

TABLE 6

| Group | Control group (Physical rub) | Experimental group (Film of the present disclosure) |
|---|---|---|
| Experimental manner | An endoscopic surgery was used, and a small hole was created at the chest, and then a small hole was created at the chest, and gauze was placed in the hole to rub the parietal pleura to permute lung lobe adhesion. | An endoscopic surgery was used, and a small hole was created at the chest, and then a small hole was created at the chest, and the film of the present disclosure was placed in the hole to spread and cover the upper brim of the lung lobe. |
| Number of animal | 4 animals were used in each experiment, and after 3 months the animal were sacrificed and an observation for adhesion strength was performed. Landrace pigs; feeding for 3 months after the implantation | 4 animals were used in each experiment, and after 3 months the animal were sacrificed and an observation for adhesion strength was performed. |

(2) Animal Experiment of Implanting a Film to a Lung Lobe of Pig

Since the film prepared by the present disclosure is soft and easy to operate, the film could perfectly fit on the surface of the lung lobe of pig (FIG. 7).

Figure 7A:
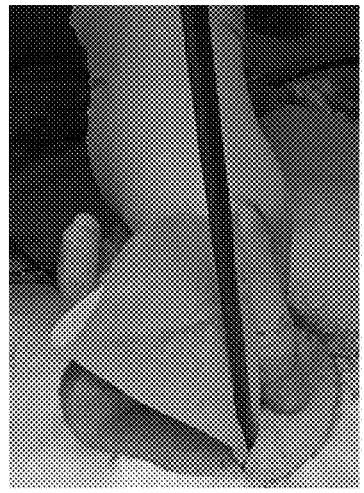
FIG. 7A shows photographs of the operation for implanting a film of the present disclosure and day 0 of implantation of the film in the experimental group in an animal experiment involving pleurodesis of a pig.
Figure 7A:
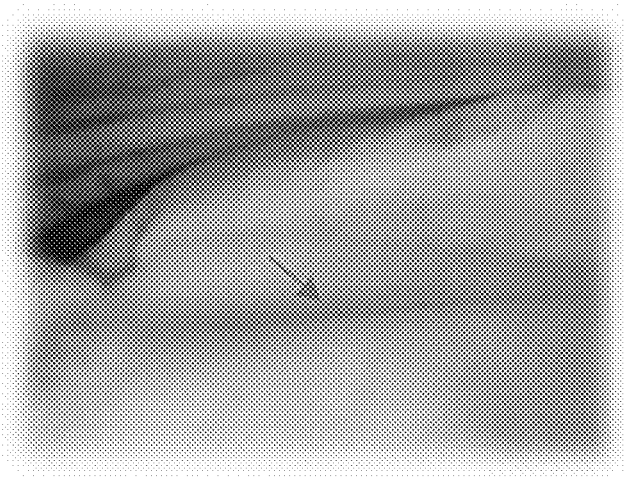
Figure 7B:
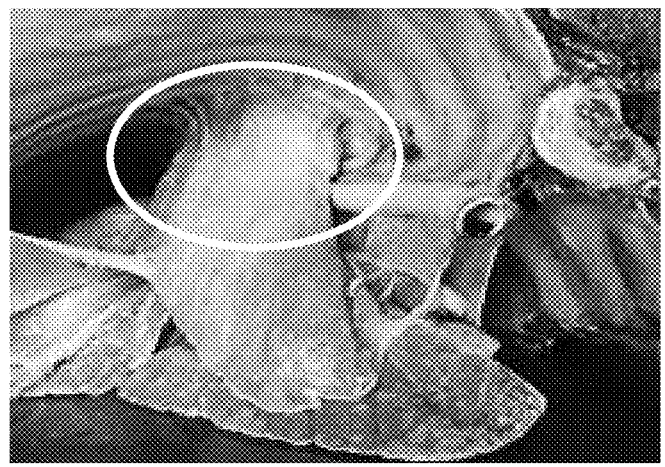
FIG. 7B shows a photograph of the experimental group 3 months after implanting the film of the present disclosure in an animal experiment involving pleurodesis of a pig.
Figure 7C:
FIG. 7C shows a photograph of the control group 3 months after implanting gauze of the present disclosure in an animal experiment involving pleurodesis of a pig.
Figure 8:
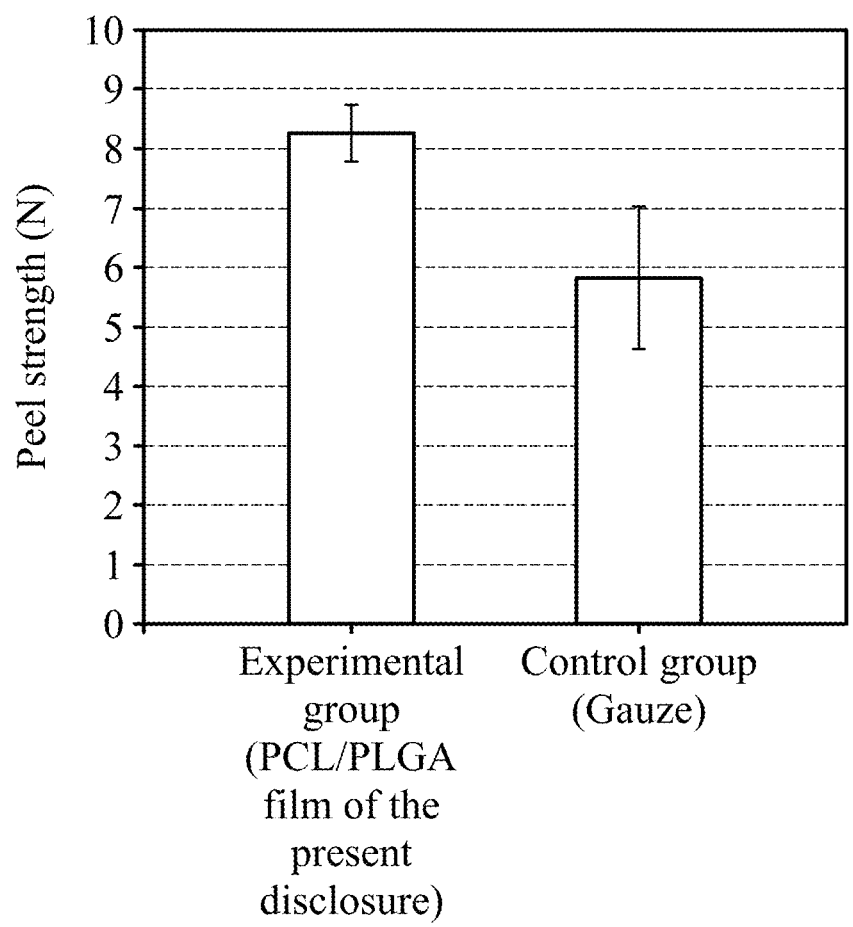
FIG. 8 shows peel strengths of pleura from lung lobes of the experimental group (a film of the present disclosure is implanted) and the control group (gauze is implanted) after 3 months.

After 90 days, the adhesion levels for the experimental group and the control group were analyzed. According to FIG. 7B and FIG. 7C, it was known that the polycaprolactone/poly(lactic-co-glycolic acid) film (FIG. 7B) was very easy to operate, and the adhesion level thereof was better than that of the control group (FIG. 7C).

After 3 months, the pigs were sacrificed to observe peel strengths of pleura from lung lobes of the experimental group and the control group. The results are shown in FIG. 7. Based on FIG. 7, it is known that the peel strength of 8.2 N of the experimental group is greater than that of 5.8 N of the control group.

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:

1. A non-fibrous porous film, which is manufactured by a method for manufacturing a non-fibrous porous film, wherein the method for manufacturing a non-fibrous porous film comprises:
preparing a polymer mixture solution, wherein the polymer mixture solution comprises:
polycaprolactone (PCL); and
at least one hydrophobic polymer, which is selected from a group consisting of polylactic acid (PLA), poly(lactic-co-glycolic acid) (PLGA), poly(glycolic acid) (PGA), polyhydroxybutyrate (PHB), polydioxanone (PDS), poly(propylene fumarate) (PPF), polyanhydrides, polyacetals, poly(ortho esters), polycarbonates, polyurethanes, polyphosphazenes and polyphosphoester, wherein the molecular weight of the at least one hydrophobic polymer is 10K-800K;
adding solid particles as a dispersing agent to the polymer mixture solution and mixing the solid particles with the polymer mixture solution, wherein the amount of solid particles added is enough to convert the polymer mixture solution into a solid mixture, wherein the particle size of the solid particles is 50-250 μm;
drying the solid mixture to form a film; and
washing the film with a washing fluid to remove the solid particles from the film to form a porous film,
wherein the weight ratio of the polycaprolactone to the at least one hydrophobic polymer is 1:0.1 to 1:10, and wherein the weight ratio of the polycaprolactone and the at least one hydrophobic polymer to solid particles is 1:0.01 to 1:250, and
wherein the real density of the non-fibrous porous film is $1.5\text{-}5.0 \times 10^{-3}$ g/cm$^2$.

2. The non-fibrous porous film as claimed in claim 1, wherein the porosity of the non-fibrous porous film is 80-99%.

3. The non-fibrous porous film as claimed in claim 1, wherein the thickness of the non-fibrous porous film is 10-1000 μm.

4. The non-fibrous porous film as claimed in claim 1, wherein the at least one hydrophobic polymer is poly(lactic-co-glycolic acid), and the solid particles are sodium chloride particles.

5. The non-fibrous porous film as claimed in claim 4, wherein the weight ratio of the polycaprolactone to the poly(lactic-co-glycolic acid) is 1:0.1 to 10, and the weight ratio of the polycaprolactone and the poly(lactic-co-glycolic acid) to the sodium chloride particle is 1:0.01 to 250.

6. The non-fibrous porous film as claimed in claim 1, wherein the polymer mixture solution further comprises at least one hydrophobic drug, wherein the weight ratio of the polycaprolactone, the at least one hydrophobic polymer and the at least one hydrophobic drug to solid particles is 1:0.5 to 10.

7. The non-fibrous porous film as claimed in claim 6, wherein the weight ratio of the polycaprolactone to the at least one hydrophobic drug is 1:0.05 to 5.

8. The non-fibrous porous film as claimed in claim 6, wherein the at least one hydrophobic drug comprises citral, nitrogen mustard, cisplatin, paclitaxel or a combination thereof.

9. The non-fibrous porous film as claimed in claim 6, wherein the at least one hydrophobic polymer is poly(lactic-co-glycolic acid), the at least one hydrophobic drug is citral, and the solid particles are sodium chloride particles.

10. A non-fibrous porous film, which is composed of a polymer mixture, wherein the polymer mixture comprises:
    polycaprolactone; and
    at least one hydrophobic polymer, which is selected from a group consisting of polylactic acid (PLA), poly (lactic-co-glycolic acid (PLGA), poly(glycolic acid) (PGA), polyhydroxybutyrate (PHB), polydioxanone (PDS), poly(propylene fumarate) (PPF), polyanhydrides, polyacetals, poly(ortho esters), polycarbonates, polyurethanes, polyphosphazenes and polyphosphoester, wherein the molecular weight of the at least one hydrophobic polymer is 10K-800K,
    wherein the weight ratio of the polycaprolactone to the at least one hydrophobic polymer is 1:0.1 to 10, and wherein the porosity of the non-fibrous porous film is 80-99%, and the roughness of the non-fibrous porous film is 10-500 μm,
    wherein the real density of the non-fibrous porous film is $1.5$-$5.0 \times 10^{-3}$ g/cm$^2$.

11. The non-fibrous porous film as claimed in claim 10, wherein the thickness of the non-fibrous porous film is 10-1000 μm.

12. The non-fibrous porous film as claimed in claim 10, wherein the at least one hydrophobic polymer is poly(lactic-co-glycolic acid).

13. The non-fibrous porous film as claimed in claim 12, wherein the weight ratio of the polycaprolactone to the poly(lactic-co-glycolic acid) is 1:0.1 to 10.

14. The non-fibrous porous film as claimed in claim 10, wherein the polymer mixture further comprises at least one hydrophobic drug, wherein the weight ratio of the polycaprolactone, the at least one hydrophobic polymer and the at least one hydrophobic drug to solid particles is 1:0.5 to 10.

15. The non-fibrous porous film as claimed in claim 14, wherein the weight ratio of the polycaprolactone to the at least one hydrophobic drug is 1:0.05 to 5.

16. The non-fibrous porous film as claimed in claim 14, wherein the at least one hydrophobic drug comprises citral, nitrogen mustard, cisplatin, paclitaxel or a combination thereof.

17. The non-fibrous porous film as claimed in claim 14, wherein the at least one hydrophobic polymer is poly(lactic-co-glycolic acid), the at least one hydrophobic drug is citral, and the solid particles are sodium chloride particles.

18. A method for tissue adhesion, comprising:
    applying the non-fibrous porous film as claimed in claim 1 to a location in a body which needs tissues to adhere to each other to promote tissue-adhesion.

19. The method for tissue adhesion as claimed in claim 18, wherein the thickness of the non-fibrous porous film is 10-1000 μm.

20. The method for tissue adhesion as claimed in claim 18, wherein the at least one hydrophobic polymer is poly (lactic-co-glycolic acid).

21. The method for tissue adhesion as claimed in claim 18, wherein the polymer mixture solution or the polymer mixture further comprises at least one hydrophobic drug, wherein the weight ratio of the polycaprolactone to the at least one hydrophobic drug is 1:0.05 to 5.

22. The method for tissue adhesion as claimed in claim 21, wherein the at least one hydrophobic drug comprises citral, nitrogen mustard, cisplatin, paclitaxel or a combination thereof.

23. The method for tissue adhesion as claimed in claim 21, wherein the at least one hydrophobic polymer is poly (lactic-co-glycolic acid), and the at least one hydrophobic drug is citral.

24. A method for tissue adhesion, comprising:
    applying the non-fibrous porous film as claimed in claim 10 to a location in a body which needs tissues to adhere to each other to promote tissue-adhesion.

* * * * *